(12) United States Patent
Chang et al.

(10) Patent No.: US 7,718,655 B2
(45) Date of Patent: May 18, 2010

(54) TRISUBSTITUTED TRIAZINE COMPOUNDS, AND METHODS FOR MAKING AND USING THE COMPOUNDS, WHICH HAVE ANTITUBULIN ACTIVITY

(75) Inventors: Young-Tae Chang, New York, NY (US); Alexander Schier, New York, NY (US); Ho-Sang Moon, New York, NY (US); Eric Jacobson, Forest Hills, NY (US); Puja Parikh, Williston Park, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 10/465,815

(22) Filed: Jun. 20, 2003

(65) Prior Publication Data

US 2004/0122009 A1 Jun. 24, 2004

Related U.S. Application Data

(63) Continuation of application No. 10/267,043, filed on Oct. 9, 2002, now abandoned.

(60) Provisional application No. 60/328,422, filed on Oct. 12, 2001.

(51) Int. Cl.
  *C07D 251/70* (2006.01)
  *A61K 31/53* (2006.01)
  *A61P 35/00* (2006.01)

(52) U.S. Cl. ................. 514/245; 544/196; 544/197; 544/206; 544/219

(58) Field of Classification Search ................. 544/196, 544/197, 206, 219; 514/241, 245
See application file for complete search history.

(56) References Cited

U.S. PATENT DOCUMENTS

| | | | |
|---|---|---|---|
| 2,508,323 A | | 5/1950 | Adams et al. |
| 2,885,400 A | | 5/1959 | Schock |
| 3,156,690 A | * | 11/1964 | Dexter et al. ............... 544/211 |
| 4,963,363 A | * | 10/1990 | Forssen ....................... 424/450 |
| 5,062,882 A | * | 11/1991 | Newton et al. ............. 504/225 |
| 6,150,360 A | * | 11/2000 | Daeyaert et al. ......... 514/236.2 |
| 6,150,362 A | | 11/2000 | Henkin et al. |
| 6,262,053 B1 | * | 7/2001 | Uckun et al. ............... 514/245 |
| 6,372,729 B1 | | 4/2002 | Daeyaert et al. |
| 7,163,943 B2 | * | 1/2007 | Timmer et al. ............. 514/241 |
| 2002/0103195 A1 | * | 8/2002 | Bonham et al. ........... 514/236.2 |
| 2003/0109529 A1 | * | 6/2003 | Hacker et al. ............... 514/241 |

FOREIGN PATENT DOCUMENTS

| | | | |
|---|---|---|---|
| CH | 337019 | * | 4/1959 |
| CH | 638376 | * | 9/1983 |
| EP | 0933 376 A2 | | 8/1999 |
| WO | WO 98/05961 A1 | | 2/1998 |
| WO | WO 98/16508 A2 | | 4/1998 |
| WO | WO 98/48551 A1 | | 10/1998 |
| WO | WO 99/31088 A1 | | 6/1999 |
| WO | WO-01/47897 A1 | * | 7/2001 |

OTHER PUBLICATIONS

Cecil Textbook of Medicine, edited by Bennet, J.C., and Plum F., 20th edition, vol. 1, 1004-1010, 1996.*
Wood et al., Current opinion in Pharmacology 1: 370-377, 2001.*
Ruchelman et al., Biorganic & Medicinal Chemistry, 12, 795-806, 2004.*
Filippusson, et al, "Design, Synthesis and Evaluation of Biomimetic Affinity Ligands for Elastases", Journal of Molecular Rrecognition. (2000). 13:370-381.
Gustafson, et al, "Incorporation of Carbohydrates and Peptides Into Large Triazinep-Based Screening Libraries Using Automated Parallel Synthesis", Tetrahedron (1998). 54:4051-4065.
Hajduk et al, "Novel Inhibitors of Erm Methyltransferases From NMR and Parallel Synthesis", J. Med. Chem. (1999). 42:3852-3859.
Johnson, et al, "Libraries of N-Alkylaminoheterocycles From Nucleophilic Aromatic Substitution With Purification by Solid Supported Liquid Extraction", Tetrahedron, (1998). 54:4097-4106.
Masquelin, et al, "Solution and Solid-Phase Synthesis of Combinatorial Libraries of Trisubstituted 1,3,5-Triazines", Heterocycles, (1998). 48(12):2489-2505.
Scharn, et al, "Spatially Addressed Synthesis of Amino- and Amino-Oxy-Substituted 1,3,5-Triazine Arrays of Polymeric Membranes", J. Comb. Chem., (12000). 2:361-369.
Silen, et al , "Screening for Novel Antimicrobials From Encoded Combinatorial Libraries by Using a Two-Dimensional Agar Format", Antimicrobial Agents and Chemotherapy, (Jun. 1998). 42(6):1447-1453.
Teng, et al, "A Strategy for the Generation of Biomimetic Ligands for Affinity Chromatography. Combinatorial Synthesis and Biological Evaluation of an IgG Binding Ligand", Journal of Molecular Recognition, (1999). 12:67-75.
Moon, H-S., et al., "A Novel Microtubule Destabilizing Entity from Orthogonal Synthesis of a Triazine Library and Zebrafish Embryo Screening", Journal of the American Chemical Society, (2002), pp. 11608-11609, vol. 124, XP002297373 ISSN: 0002-7863.

* cited by examiner

*Primary Examiner*—Venkataraman Balasubramanian
(74) *Attorney, Agent, or Firm*—Browdy and Neimark, PLLC

(57) ABSTRACT

Trisubstituted triazines can be synthesized from cyanuric chloride. These compounds are useful anti-tubulin agents for treating cancer and proliferative diseases.

2 Claims, 3 Drawing Sheets

DMSO Control

Myoseverin

S84

TRISUBSTITUTED TRIAZINE COMPOUNDS, AND METHODS FOR MAKING AND USING THE COMPOUNDS, WHICH HAVE ANTITUBULIN ACTIVITY

CROSS REFERENCE TO RELATED APPLICATION

The present application is a Continuation of prior Application No. 10/267,043, filed Oct. 9, 2002, and now abandoned and claims priority from non-provisional application Ser. No. 60/328,422, filed Oct. 12, 2001, the entire contents of which are hereby incorporated by reference.

FIELD OF THE INVENTION

The present invention relates to trisubstituted triazine compounds which can be used as anticancer drugs. The present invention also relates to methods for making these trisubstituted triazine compounds.

BACKGROUND OF THE INVENTION

Cancers are among the leading causes of death in animals and humans. Although many types of chemotherapeutic agents have been shown to be effective against cancers and tumor cells, not all types of cancers and tumors respond to these agents. Current major chemotherapeutic and radiation therapy regimens focus on inducing DNA damage which indiscriminately kills cells, with the hope that the cancerous cells die more quickly than the normal cells. Unfortunately, in many cases the end result is simply prolonged suffering because DNA damage accumulates too quickly in the body for the patient to handle.

Microtubules are an array of fibrous cytoskeleton proteins which control cell strength and molecular movement within the cell. In particular, microtubules are critical to chromosomal movement during cell division. Microtubules are comprised of tubulin subunits which form a diverse array of both permanent and transient structures. The processes of microtubule assembly and disassembly are dynamic and can be affected by various factors including temperature, anti-cancer drug such as colchicines and taxol, and microtubule-associated proteins (MAPs). MAPs are involved in the formation and stabilization of microtubules.

It is hoped that tubulin-binding drugs will offer an alternative to indiscriminate cellular destruction. For mitosis to succeed, the cellular cytoskeleton must be completely rearranged in a particular manner. In fact, it is microtubular motion that is responsible for the actual separation and division of the cellular compartments and the correct distribution of DNA between two cells. Interruption of this process can halt mitosis without any inherent cytotoxic effect, although prolonged interruption of mitosis can lead to apoptosis.

Microtubule formation is a dynamic process which includes polymerization of α- and β-tubulin heterodimers and degradation of tubular polymers. Tubulin-binding drugs interfere with this dynamic process, either by inhibiting microtubule assembly or by over-stabilizing the polymer structure. Microtubule assembly inhibitors are conventionally divided into two classes: colchicines, domain binders such as podophyllotoxin, steganacin, combretastain, and amphethinile; and vinca alkaloid domain binders such as vinblastine, vincristine, maytansinoid, phomopsin A, rhizoxin, dolastatin, and cryptophycin. Taxol microtubule-stabilizing compounds, obtained from natural products, include epothilone, eleutherobin, and discodermolide.

The vinca alkaloids, including vinblastine and vincristine, have been used for treating cancers such as leukemias and lymphomas for a long time, and taxol derivatives have recently been used for treating breast cancers. However, several problems remain with these conventional anti-tubulin drugs. Among these problems are inherent toxicity (especially neurotoxicity) as a side effect, low solubility of the compounds, availability in quantity, and multi-drug resistance. As most of the lead compounds originated from naturally occurring sources (plants, sponges, mollusks, bacteria), chemical modification might be a straightforward approach for improving the activity and properties of the drugs while reducing side effects. Serious efforts have been made to synthesize derivatives of vinca alkaloids, colchicines, taxol and related compounds, but modification of the complicated natural products without adversely affecting utility has so far been difficult.

Many other natural products and their synthetic derivatives are also undergoing clinical testing, particularly combrestatins and cryptophycines, which elicit much interest because of their anti-angiogenic activity and high activity (pM IC50) with respect to multi-drug resistant cells. Another approach is to screen small synthetic molecules to find novel tubulin binders.

Myoseverin, a recently discovered tubulin binder with a novel purine structure, has so far demonstrated a promising ability to surmount the major problems associated with currently available tubulin binding drugs. Myoseverin was originally isolated from a library of 2, 6, 9-substitued purines by virtue of its activity of inducing the reversible fission of multinucleated myotubes into fragments. While myoseverin has an in vitro tubulin depolymerization effect and tumor cell growth inhibition without an apparent cytotoxicity, a transcriptional profiling using DNA microarray and biochemical analysis indicated that myoseverin affects expression of a variety of growth factors, immunomodulation, intracellular matrix remodeling, and stress response genes, implicating the activation of biochemical pathways involved in wound healing. The moderate activity of myoseverin (low μM $IC_{50}$) remains to be improved by structure-activity relationships.

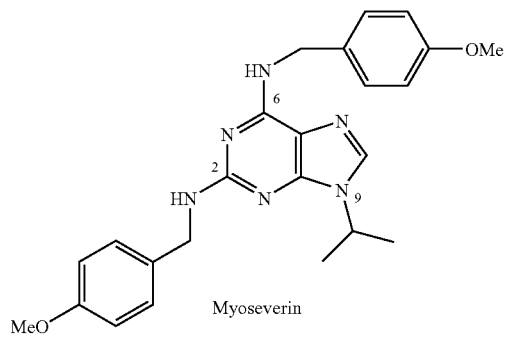

Figure 1

Myoseverin

Although a 2,6,9-substituted purine library is a useful tool for developing better derivatives of myoseverin, there are several flaws. The synthetic scheme confined the modification sequence to substitution at the 9-position (Mitsunobu reaction), the 6-position ($1^{st}$ amination) and the 2-position ($2^{nd}$ amination) because of the reactivity differences among the three positions. This sequence and reaction nature limit the flexibility of diversity generation, especially for the 9- and 6-positions. Additionally, purine, the starting material, is relatively expensive.

SUMMARY OF THE INVENTION

It is an object of the present invention to overcome the aforesaid deficiencies in the prior art.

It is another object of the present invention to provide anti-tubulin agents.

It is a further object of the present invention to provide methods to synthesize trisubstituted triazine anti-tubulin agents.

It is yet another object of the present invention to provide methods and compositions for treating cancer.

The present invention provides novel trisubstituted triazines. A novel triazine library was designed using computer aided modeling and known structure-activity relationships data from myoseverin derivatives. The triazine scaffold has three-fold symmetry, so that the modification is much more flexible than in purine. Furthermore, the starting material, cyanuric chloride, and all of the required building blocks (amines) and reagents (simple bases) are inexpensive. Another significant advantage over other natural product derivatives is the ease with which the scaffold can be modified, as all of the building blocks are modular.

The trisubstituted triazine compounds of the present invention have the following structure:

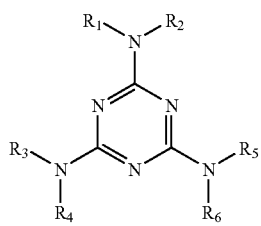

wherein $R_1$, is H or $C_1$-$C_{20}$ alkyl, phenyl substituted with at least one of F, Cl, methoxy, ethoxy, trifluoromethyl, and $C_1$-$C_6$ alkyl, or benzyl substituted with at least one of F, Cl, methoxy, ethoxy, trifluoromethyl, and $C_1$-$C_6$ alkyl;

$R_2$, $R_3$, $R_4$, $R_5$ and $R_6$ are $C_1$-$C_{20}$ alkyl, phenyl substituted with at least one of F, Cl, methoxy, ethoxy, trifluoromethyl, and $C_1$-$C_6$ alkyl, or benzyl substituted with at least one of F, Cl, methoxy, ethoxy, trifluoromethyl, and $C_1$-$C_6$ alkyl.

Other compounds according to the present invention include compounds of the formula:

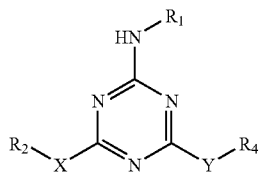

wherein $R_1$ is $C_1$-$C_{20}$ alkyl, phenyl substituted with at least one of F, Cl, methoxy, ethoxy, trifluoromethyl, and $C_1$-$C_6$ alkyl, or benzyl substituted with at least one of F, Cl, methoxy, ethoxy, trifluoromethyl, and $C_1$-$C_6$ alkyl;

$R_2$, $R_3$, $R_4$ and $R_5$ are $C_1$-$C_{20}$ alkyl, phenyl substituted with at least one of F, Cl, methoxy, ethoxy, trifluoromethyl, and $C_1$-$C_6$ alkyl, or benzyl substituted with at least one of F, Cl, methoxy, ethoxy, trifluoromethyl, $C_1$-$C_6$ alkyl, and saturated or unsaturated heterocyclic rings having from three to seven-membered rings containing at least one of N, O, or S;

X is $NR_3$, O, or S;

Y is $NR_5$, O, or S.

The structure-activity relationships of myoseverin were analyzed, and it was found that the presence of 4-methoxybenzyl at both the 2- and 6-positions was critical for the activity. An alkyl group at the $N_9$ position allowed for modification with varied activities. From this it was deduced that properly oriented methoxyphenyl groups form an important binding motif for tubulin activity. This information was used to design a library using a triazine scaffold as a possible tubulin depolymerization reagent.

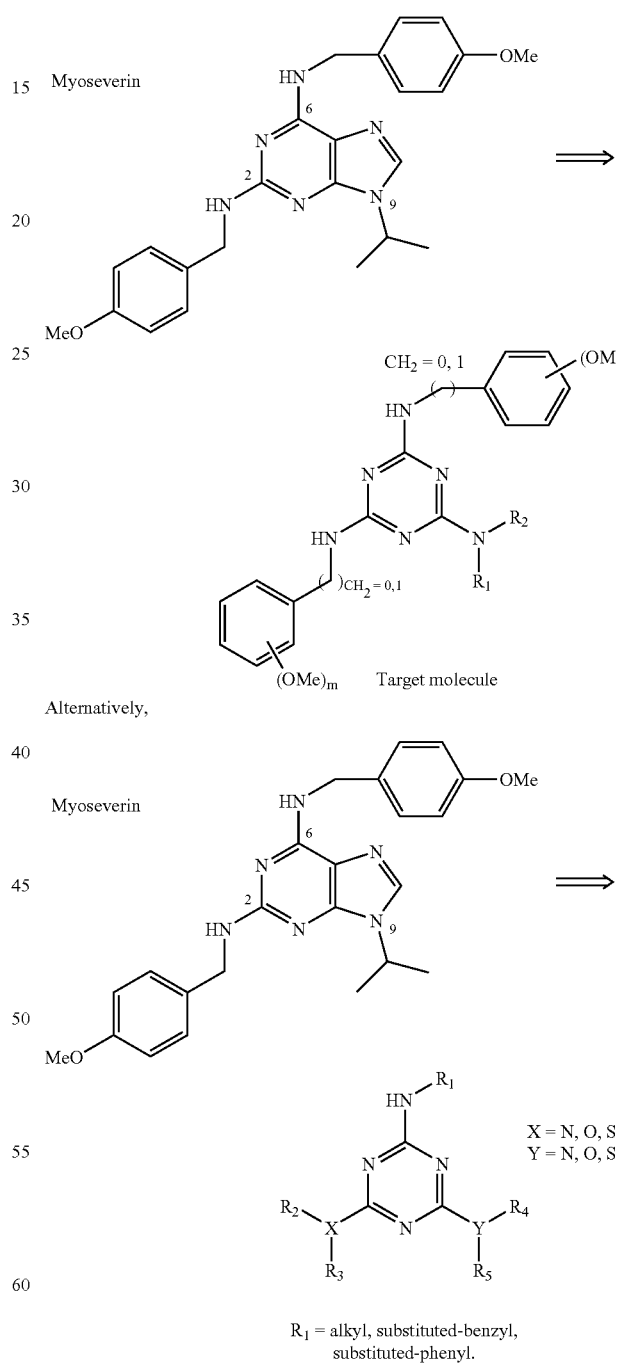

wherein $R_1$ is $C_1$-$C_{20}$ alkyl, phenyl substituted with at least one of F, Cl, methoxy, ethoxy, trifluoromethyl, and $C_1$-$C_6$ alkyl, or benzyl substituted with at least one of F, Cl, methoxy, ethoxy, trifluoromethyl, and $C_1$-$C_6$ alkyl;

$R_2$, $R_3$, $R_4$ and $R_5$ are $C_1$-$C_{20}$ alkyl, phenyl substituted with at least one of F, Cl, methoxy, ethoxy, trifluoromethyl, and $C_1$-$C_6$ alkyl, or benzyl substituted with at least one of F, Cl, methoxy, ethoxy, trifluoromethyl, $C_1$-$C_6$ alkyl, and saturated or unsaturated heterocyclic rings having from three to seven-membered rings containing at least one of N, O, or S;

X is $NR_3$, O, or S;

Y is $NR_2$, O, or S.

Scheme 1, shown below, illustrates a straightforward synthetic pathway which can be used for preparation of a trisubstituted triazine library.

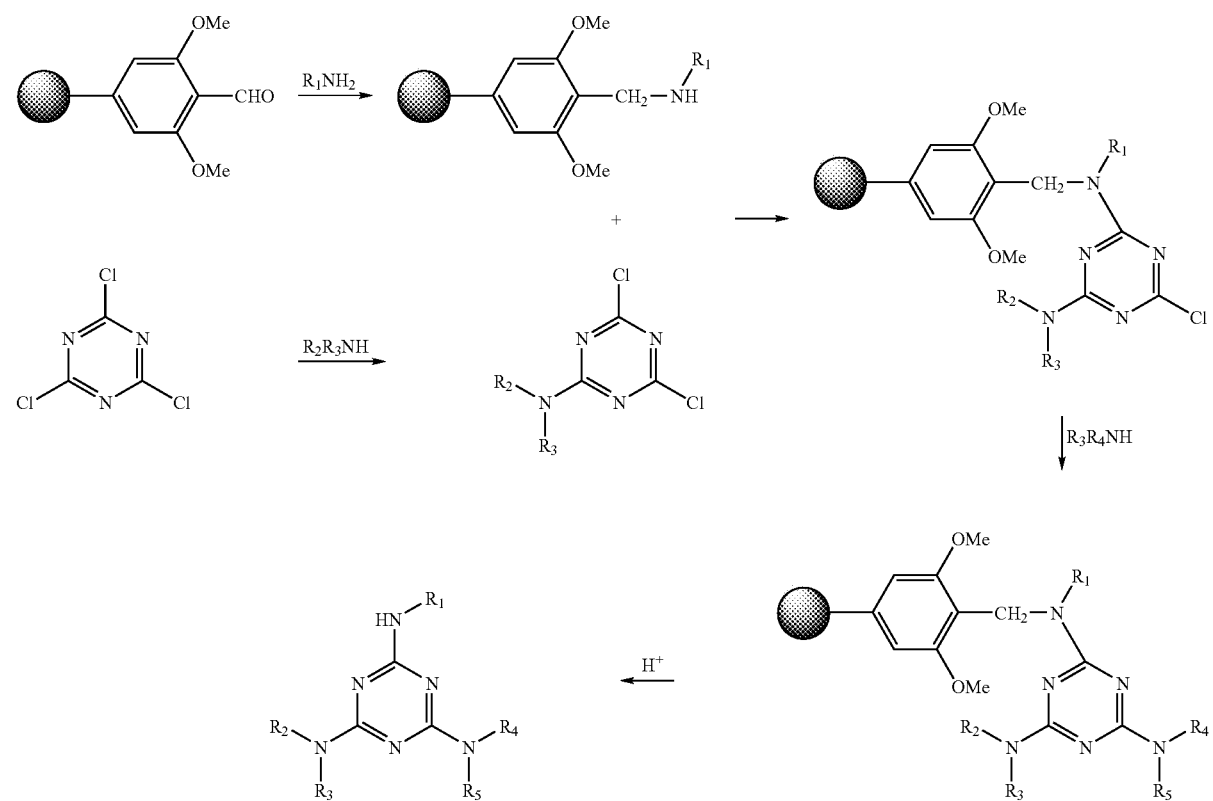

Scheme 2, shown below, illustrates a synthetic pathway for preparing another trisubstituted triazine library.

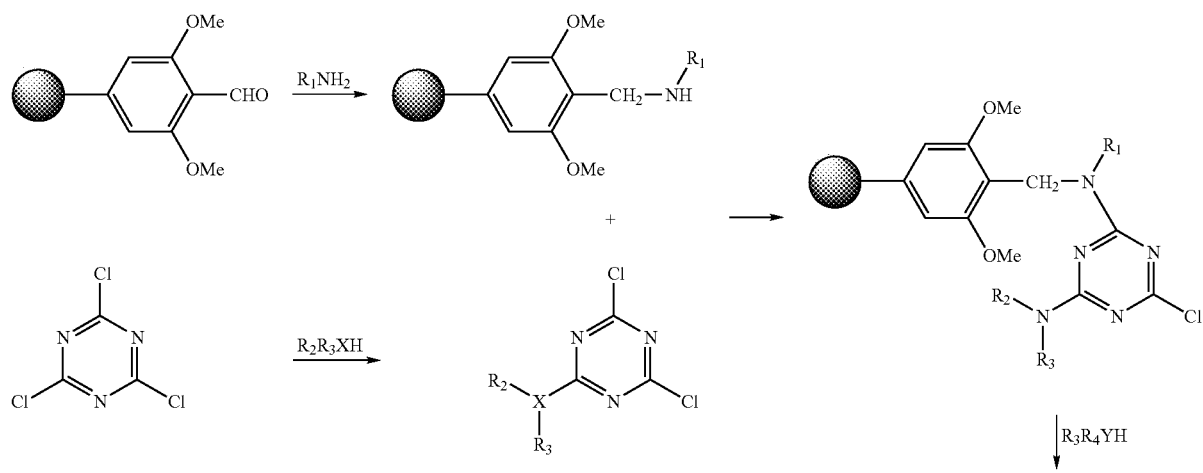

-continued

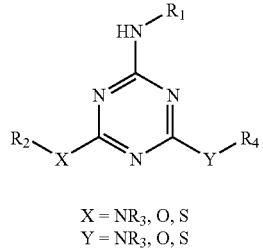

X = NR₃, O, S
Y = NR₃, O, S

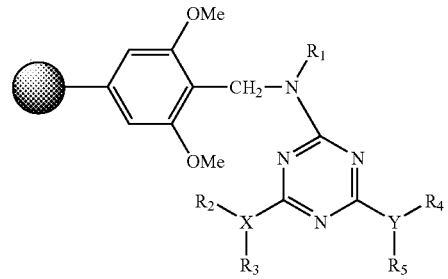

wherein $R_1$ is $C_1$-$C_{20}$ alkyl, phenyl substituted with at least one of F, Cl, methoxy, ethoxy, trifluoromethyl, and $C_1$-$C_6$ alkyl, or benzyl substituted with at least one of F, Cl, methoxy, ethoxy, trifluoromethyl, and $C_1$-$C_6$ alkyl;

$R_2$, $R_3$, $R_4$ and $R_5$ are $C_1$-$C_{20}$ alkyl, phenyl substituted with at least one of F, Cl, methoxy, ethoxy, trifluoromethyl, and $C_1$-$C_6$ alkyl, or benzyl substituted with at least one of F, Cl, methoxy, ethoxy, trifluoromethyl, $C_1$-$C_6$ alkyl, and saturated or unsaturated heterocyclic rings having from three to seven-membered rings containing at least one of N, O, or S;

X is N, O, or S;

Y is N, O, or S.

Instead of using selective amination, which requires careful monitoring of the reaction and purification, three different building blocks were used to construct the library. The first amine is loaded onto an aldehyde resin by reductive amination. The second amine was added to cyanuric chloride to form a building block with the dichlorotriazine core structure. These two building blocks are then combined by aminating the first building block onto one of the chlorine positions of the second building block. A sequential over-amination on the other chloride position is efficiently suppressed by physical segregation from other amines available on the solid support. The third building block, a primary or secondary amine, then reacts with the last chloride position to give the trisubstituted triazine. As all of the reactions are orthogonal to each other, once each reaction step is completed, no further purification is required after cleavage of the final compound under acidic conditions. The purity of all of the products was monitored by liquid chromatography-mass spectroscopy.

BRIEF DESCRIPTION OF THE DRAWINGS

FIG. 4 shows the assay result of Zebrafish embryo with:

Figure 1:
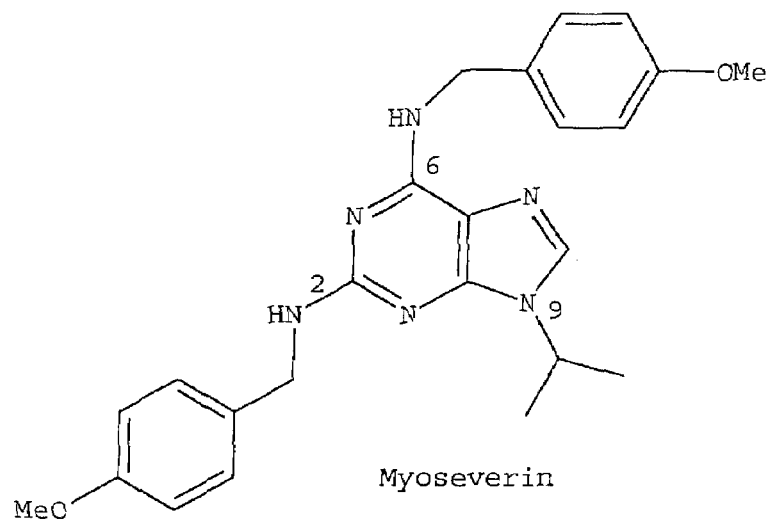
FIG. 1 shows the structure of myoseverin.
Figure 2:
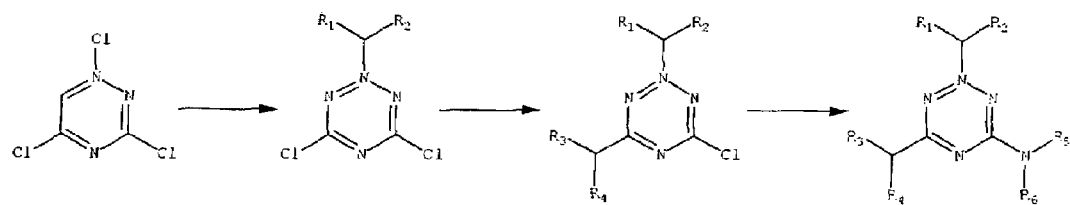
FIG. 2 is a procedure for solution phase triazine library synthesis.
Figure 3:
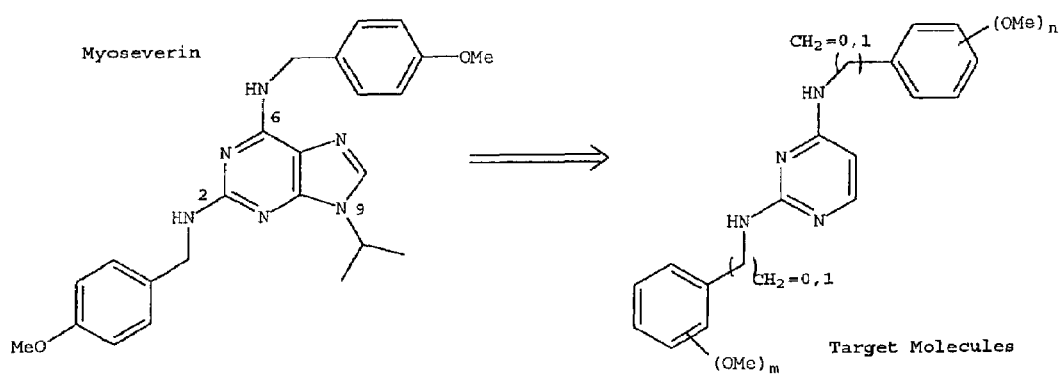
FIG. 3 illustrates design of target compounds.
Figure 4A:
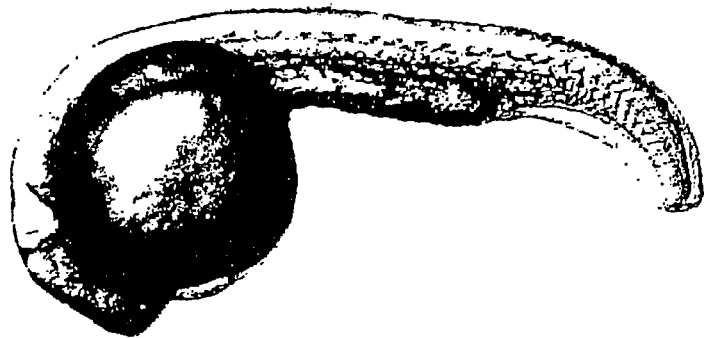
FIG. 4A, control.
Figure 4B:
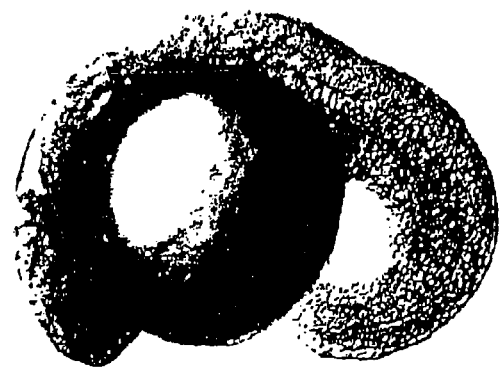
FIG. 4B, myoseverin (1 micromole)
Figure 4C:
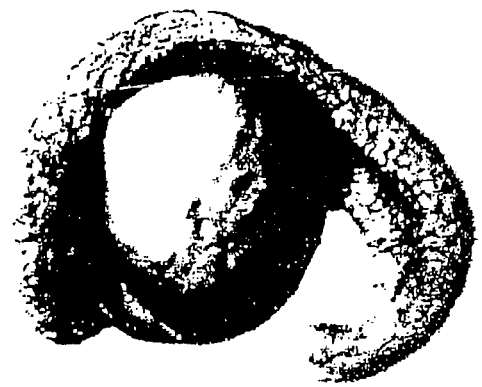
FIG. 4C, S84 (1 micromole).

As used herein, alkyl carbon chains, if not specified, contain from 1 to 20 carbon atoms, preferably from 1 to 16 carbon atoms, and are straight or branched.

As used herein an alkyl group substituent includes halo, haloalkyl, preferably halo lower alkyl, aryl, hydroxy, alkoxy, aryloxy, alkoxy, alkylthio, arylthio, aralkyloxy, aralkylthio, carboxy, alkoxycarbonyl, oxo, and cycloalkyl.

For the present invention, "cyclic" refers to cyclic groups preferably containing from 3 to 19 carbon atoms, preferably 3 to 10 members, more preferably 5 to 7 members. Cyclic groups include hetero atoms, and may include bridged rings, fused rings, either heterocyclic, cyclic, or aryl rings.

The term "aryl" herein refers to aromatic cyclic compounds having up to 10 atoms, including carbon atoms, oxygen atoms, sulfur atoms, selenium atoms, etc. Aryl groups include, but are not limited to, groups such as phenyl, substituted phenyl, naphthyl, substituted naphthyl, in which the substituent is preferably lower alkyl, halogen, or lower alkyl. "Aryl" may also refer to fused rings systems having aromatic unsaturation. The fused ring systems can contain up to about 7 rings.

An "aryl group substituent" as used herein includes alkyl, cycloalkyl, cycloaryl, aryl, heteroaryl, optionally substituted with 1 or more, preferably 1 to 3, substituents selected from halo, haloalkyl, and alkyl, arylalkyl, heteroarylalkyl, alkenyl containing 1 to 2 double bonds, alkynyl containing 1 to 2 triple bonds, halo, hydroxy, polyhaloalkyl, preferably trifluoromethyl, formyl, alkylcarbonyl, arylcarbonyl, optionally substituted with 1 or more, preferably 1 to 3, substituents selected from halo, haloalkyl, alkyl, heteroarylcarbonyl, carboxyl, alkoxycarbonyl, aryloxycarbonyl, aminocarbonyl, alkylaminocarbonyl, dialkylaminocarbonyl, arylalkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, amido, nitro, mercapto, alkylthio, arylthio, perfluoroalkylthio, thiocyano, isothiocyano, alkylsufinyl, alkylsulfonyl, arylsulfinyl, arylsulfonyl, aminosulfonyl, alkylaminosulfinyl, dialkylaminosulfonyl, and arylaminosulfonyl.

The term "arylalkyl" as used herein refers to an alkyl group which is substituted with one or more aryl groups. Examples of arylalkyl groups include benzyl, 9-fluorenylmethyl, naphthylmethyl, diphenylmethyl, and triphenylmethyl.

"Cycloalkyl" as used herein refers to a saturated mono- or multicyclic ring system, preferably of 3 to 10 carbon atoms, more preferably from 3 to 6 carbon atoms.

The term "heteroaryl" for purposes of the present application refers to a monocyclic or multicyclic ring system, preferably about 5 to about 15 members, in which at least one atom, preferably 1 to 3 atoms, is a heteroatom, that is, an element other than carbon, including nitrogen, oxygen, or sulfur atoms. The heteroaryl may be optionally substituted with one or more, preferably 1 to 3, aryl group substituents. Exemplary heteroaryl groups include, for example, furanyl, thienyl, pyridyl, pyrrolyl, N-methylpyrrolyl, quinolyinyl and isoquinolinyl.

The term "heterocyclic" refers to a monocyclic or multicyclic ring system, preferably of 3 to 10 members, more preferably 4 to 7 members, where one or more, preferably 1 to 3, of the atoms in the ring system is a heteroatom, i.e., an atom that is other than carbon, such as nitrogen, oxygen, or sulfur. The heterocycle may be optionally substituted with one or more, preferably 1 to 3, aryl group substituents. Preferred substituents of the heterocyclic group include hydroxy, alkoxy, halo lower alkyl. The term heterocyclic may include heteroaryl. Exemplary heterocyclics include, for example, pyrrolidinyl, piperidinyl, alkylpiperidinyl, morpholinyl, oxadiazolyl, or triazolyl.

The term "halogen" or "halide" includes F, Cl, Br, and I. This can include pseudohalides, which are anions that behave substantially similarly to halides. These compounds can be used in the same manner and treated in the same manner as halides. Pseudohalides include, but are not limited to, cyanide, cyanate, thiocyanate, selenocyanate, trifluoromethyl, and azide.

The term "haloalkyl" refers to a lower alkyl radical in which one or more of the hydrogen atoms are replaced by halogen, including but not limited to, chloromethyl, trifluoromethyl, 1-chloro-2-fluoroethyl, and the like. "Haloalkoxy" refers to RO— in which R is a haloalkyl group.

The term "sulfinyl" refers to —S(O)—. "Sulfonyl" refers to —S(O) 2—

"Aminocarbonyl" refers to —C(O)NH$_2$.

The term "arylene" as used herein refers to a monocyclic or polycyclic bivalent aromatic group preferably having from 1 to 20 carbon atoms and at least one aromatic ring. The arylene group is optionally substituted with one or more alkyl group substituents. There may be optionally inserted around the arylene group one or more oxygen, sulfur, or substituted or unsubstitued nitrogen atoms, where the nitrogen substituent is alkyl.

"Heteroarylene" refers to a bivalent monocyclic or multicyclic ring system, preferably of about 5 to about 15 members, wherein one or more of the atoms in the ring system is a heteroatom. The heteroarylene may be optionally substituted with one or more aryl group substituents.

The term "library" refers to a collection of diverse compounds. In the present case, the library is based in a triazine scoffold.

EXAMPLE 1

Scheme 3

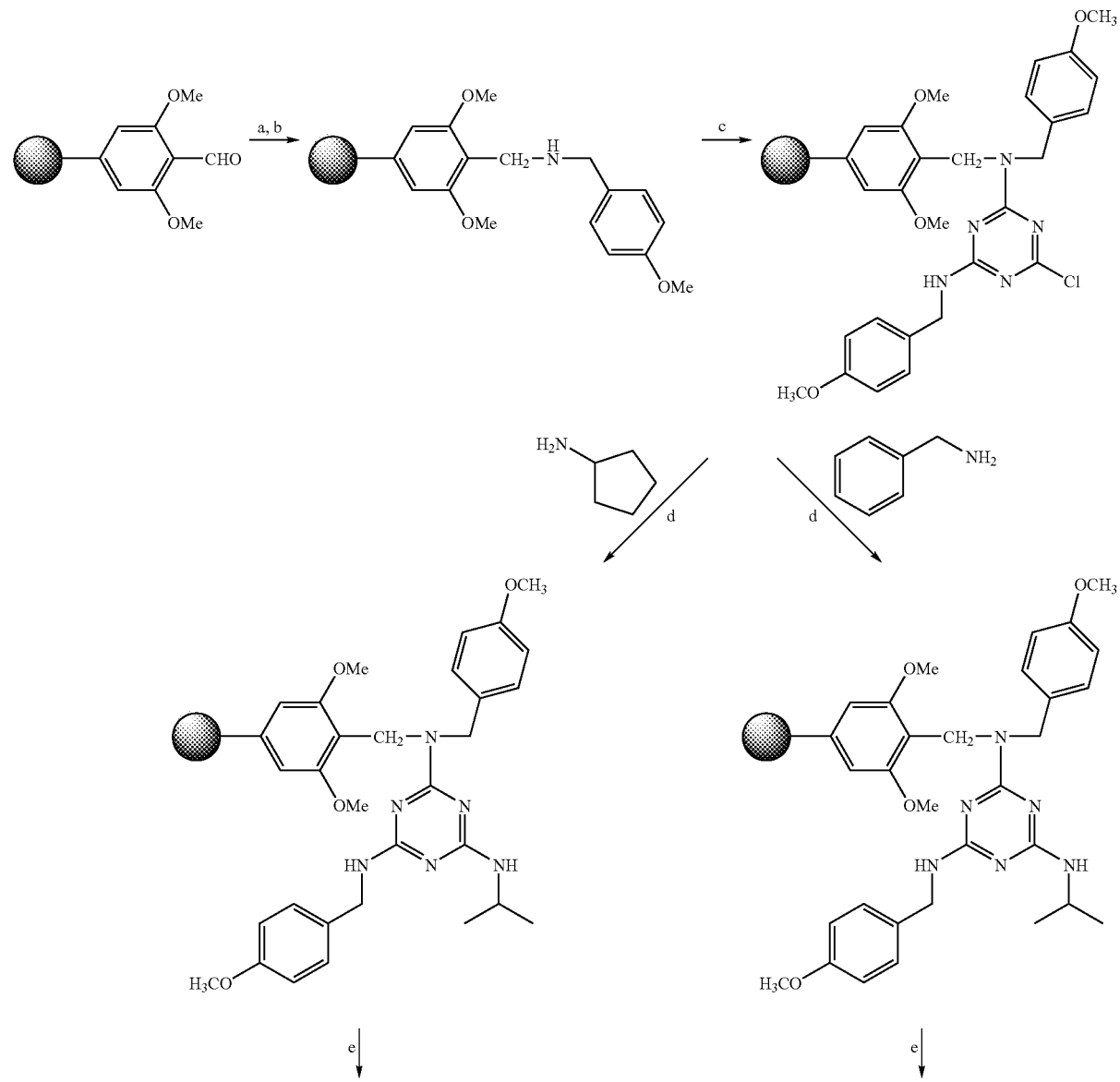

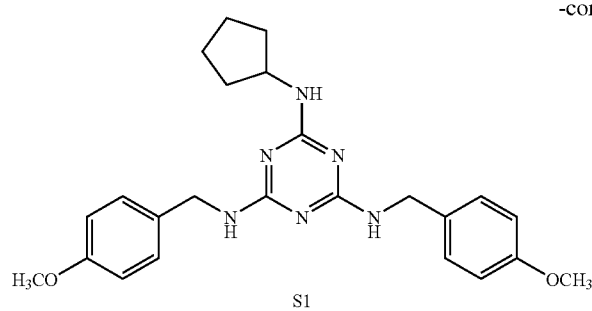

S1

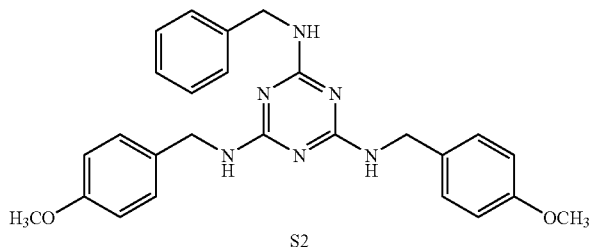

S2

Reagents: (a) 4-Methoxybenzylamine, 2% acetic acid in DMF, rt, 1 hr. (b) Sodium triacetoxyborohydride, rt, 12 hr. (c) (4,6-Dichloro-[1,3,5]triazine-2-yl)-(4-methoxybnenzyl) amine, DIEA, 60° C., 2 hr. (d) Cyclopentylamine or benzylamine, DIEA, 120° C., 2 hr. (e) 10% HCl in THF.

Syntheses of Compounds (S1-S52)

To a solution of PAL-aldehyde resin (1.0 g, 1.1 mmole, purchased from Midwest Bio-Tech, sub. 1.10, USA) was added 4-methoxybenzylamine (754 mg, 5.5 mmole, 5 eq) in anhydrous THF (50 ml, containing 10 ml of acetic acid) at room temperature. The reaction mixture was stirred for 1 min at room temperature and then sodium triacetoxyborohydride was added (1.63 g, 7.7 mmole, 7 eq). The reaction mixture was stirred for 12 hr and filtered. The resin was washed with DMF (3 times), dichloromethane (3 times), methanol (3 times), and dichloromethane (3 times).

The next step was performed by general solid phase synthesis. To a solution of resin (1.0 g) and DIEA (1 ml) in anhydrous THF (50 ml) at room temperature was added (4,6-Dichloro-[1,3,5]triazine-2-yl)-(4-methoxybenzyl)amine (1.0 g 3.5 mmole). The reaction mixture was stirred for 2 hr at 60° C. and filtered. The resin was washed with DMF (3 times), dichloromethane (3 times), methanol (3 times), and dichloromethane (3 times).

The final coupling step was performed by general solid phase synthesis. The resin (10 mg) and DIEA (0.1 ml) in NMP (0.7 ml) was added each amine (4 eq). The reaction mixture was stirred for 2 hr at 120° C. and filtered. The resin was washed with DMF (3 times), dichloromethane (3 times), methanol (3 times), and dichloromethane (3 times).

The resin cleavage reaction was performed using 5% HCl in THF for 30 min at room temperature and washed with THF. The products were identified by liquid chromatography-mass spectroscopy (Agilent 1100 model).

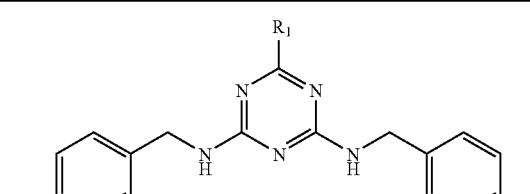

| Comp. ID | R1 | Exact Mass | Found (M + 1) |
|---|---|---|---|
| S1 |  | 434.2 | 435.1 |
| S2 | 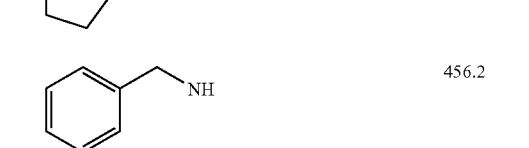 | 456.2 | 457.1 |
| S3 |  | 482.2 | 483.1 |

-continued

| Comp. ID | R1 | Exact Mass | Found (M + 1) |
|---|---|---|---|
| S4 | benzyl-N(CH3)- | 470.2 | 471.1 |
| S5 | 4-chlorobenzyl-NH- | 490.2 | 491.1 |
| S6 | 4-methylbenzyl-NH- | 470.2 | 471.1 |
| S7 | 3,4-methylenedioxybenzyl-NH- | 500.3 | 501.1 |
| S8 | 3,4-dimethoxybenzyl-NH- | 516.3 | 517.1 |
| S9 | 4-fluorobenzyl-NH- | 474.2 | 475.1 |
| S10 | 2-(trifluoromethyl)benzyl-NH- | 524.2 | 525.1 |
| S11 | 4-cyclohexylpiperazin-1-yl | 517.3 | 518.2 |
| S12 | 4-(4-nitrophenyl)piperazin-1-yl | 556.3 | 557.1 |
| S13 | 4-(pyridin-2-yl)piperazin-1-yl | 512.3 | 513.1 |
| S14 | 3,3-diphenylpropyl-N- | 560.3 | 561.2 |

-continued
| Comp. ID | R1 | Exact Mass | Found (M + 1) |
|---|---|---|---|
| S15 | 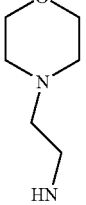 | 479.3 | 480.1 |
| S16 | 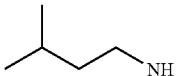 | 436.3 | 437.1 |
| S17 | 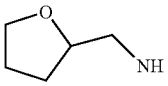 | 450.2 | 451.1 |
| S18 | 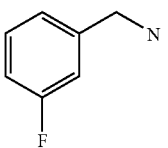 | 474.2 | 475.1 |
| S19 | 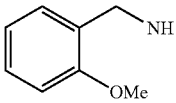 | 486.2 | 475.1 |
| S20 | 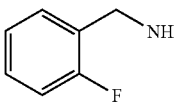 | 474.2 | 475.1 |
| S21 | 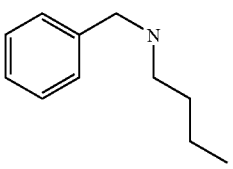 | 512.3 | 513.2 |
| S22 | 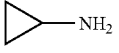 | 406.2 | 407.1 |
| S23 | 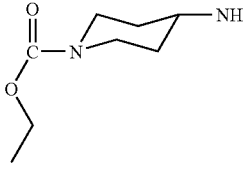 | 521.3 | 522.1 |
| S24 | 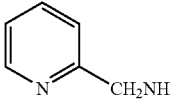 | 457.2 | 458.1 |
| S25 | 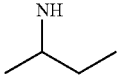 | 422.2 | 423.1 |

-continued

| Comp. ID | R1 | Exact Mass | Found (M + 1) |
|---|---|---|---|
| S26 | pyrrolidin-2-one-N-(CH2)4-NH | 490.3 | 492.1 |
| S27 | NH2CH2CH2N | 409.2 | 410.1 |
| S28 | HN-(CH2)7-CH3 | 478.3 | 479.2 |
| S29 | phenyl-CH2CH2-NH | 470.2 | 471.1 |
| S30 | HO-CH2-CH(OH)-CH2-NH | 440.2 | 441.1 |
| S31 | (CH3CH2)2CH-NH | 436.3 | 437.2 |
| S32 | 2-adamantyl-NH | 500.3 | 501.2 |
| S33 | CH3NH | 380.2 | 381.1 |
| S34 | HNCH2CH2OH | 410.2 | 411.1 |
| S35 | norbornyl-NH | 460.2 | 461.2 |
| S36 | 4-aminocyclohexyl-NH | 463.2 | 464.2 |
| S37 | 2-aminocyclohexyl-NH | 463.2 | 464.2 |
| S38 | cycloheptyl-NH | 462.2 | 463.2 |

-continued
| Comp. ID | R1 | Exact Mass | Found (M + 1) |
|---|---|---|---|
| S39 | 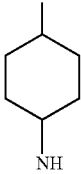 | 464.2 | 465.2 |
| S40 | 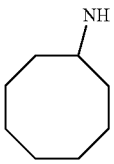 | 476.3 | 477.3 |
| S41 | 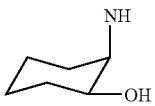 | 464.3 | 465.2 |
| S42 | 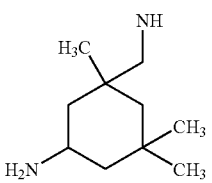 | 519.3 | 520.3 |
| S43 | 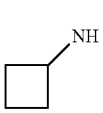 | 420.2 | 421.2 |
| S44 | 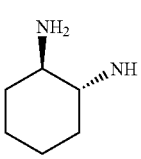 | 463.2 | 464.2 |
| S45 | 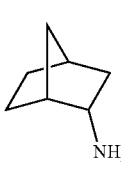 | 460.2 | 461.2 |
| S46 | 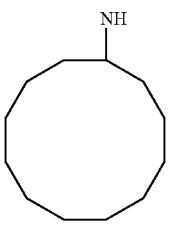 | 532.3 | 533.3 |
| S47 | 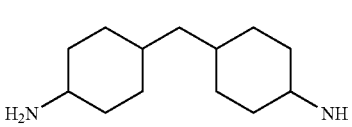 | 559.3 | 560.3 |

-continued
| Comp. ID | R1 | Exact Mass | Found (M + 1) |
|---|---|---|---|
| S48 | (cyclohexylmethyl)NH | 462.2 | 463.2 |
| S49 | (diethylamino) | 422.2 | 423.2 |
| S50 | (dibutylamino) | 478.3 | 479.3 |
| S51 | $CH_3CH_2NH$ | 394.2 | 395.1 |
| S52 | $H_2NCH_2CH_2CH_2NH$ | 423.2 | 424.2 |
EXAMPLE 2
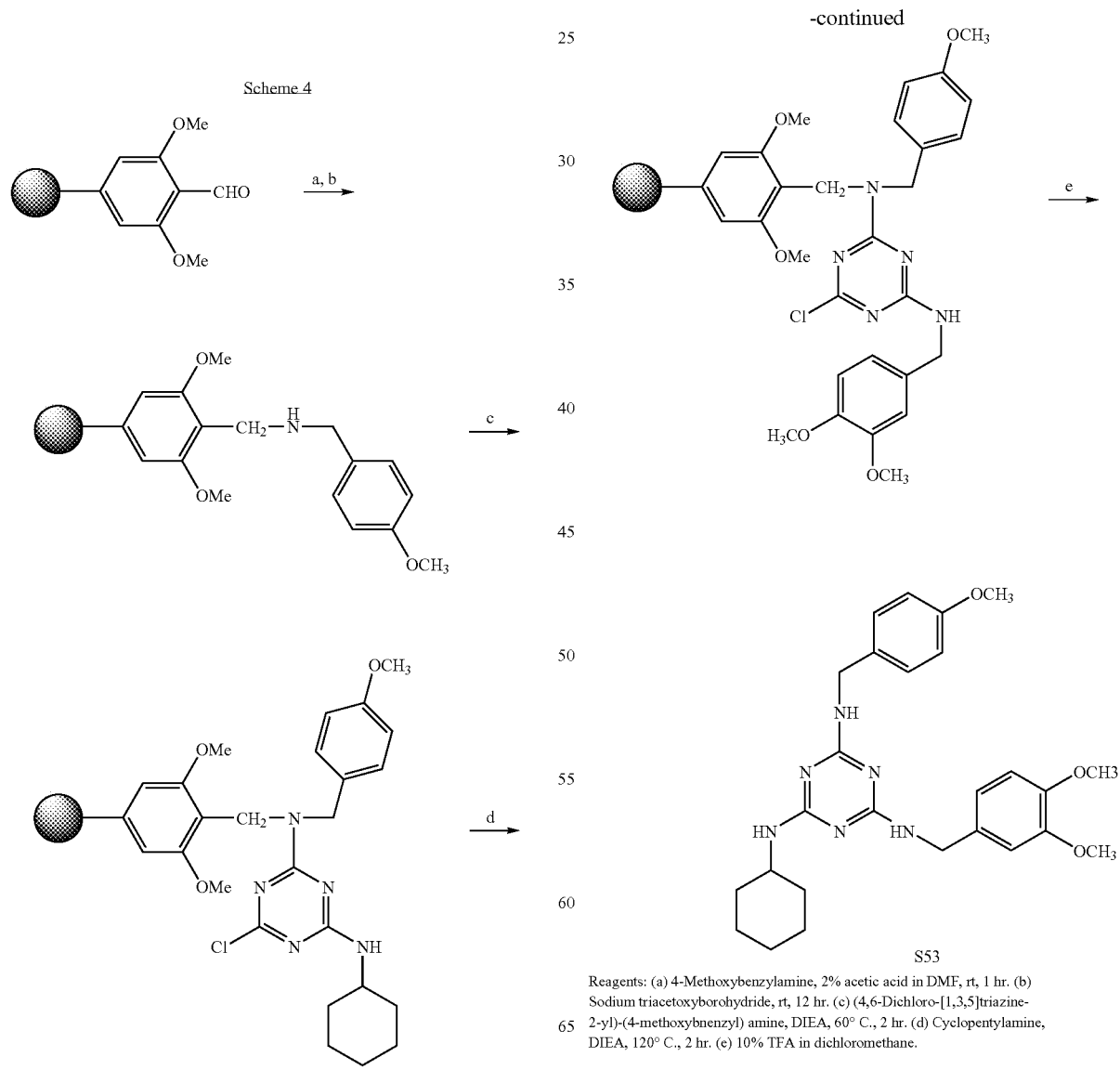
Scheme 4
Reagents: (a) 4-Methoxybenzylamine, 2% acetic acid in DMF, rt, 1 hr. (b) Sodium triacetoxyborohydride, rt, 12 hr. (c) (4,6-Dichloro-[1,3,5]triazine-2-yl)-(4-methoxybnenzyl) amine, DIEA, 60° C., 2 hr. (d) Cyclopentylamine, DIEA, 120° C., 2 hr. (e) 10% TFA in dichloromethane.

Synthesis of Compounds (S53-S66)

To a solution of PAL-aldehyde resin (1.0 g, 1.1 mmole, purchased from Midwest Bio-Tech, sub. 1.10, USA) was added 4-methoxybenzylamine (754 mg, 5.5 mmole, 5 eq) in anhydrous THF (50 ml, containing 10 ml of acetic acid) at room temperature. The reaction mixture was stirred for 1 min at room temperature and then sodium triacetoxyborohydride was added (1.63 g, 7.7 mmole, 7 eq). The reaction mixture was stirred for 12 hr and filtered. The resin was washed with DMF (3 times), dichloromethane (3 times), methanol (3 times), and dichloromethane (3 times).

The next step was performed by general solid phase synthesis. To a solution of resin (1.0 g) and DIEA (1 ml) in anhydrous THF (50 ml) at room temperature was added cyclohexyl-(4,6-dichloro-[1,3,5]triazine-2-yl)-amine (950 mg 3.5 eq). The reaction mixture was stirred for 2 hr at 60° C. and filtered. The resin was washed with DMF (3 times), dichloromethane (3 times), methanol (3 times), and dichloromethane (3 times).

The final coupling step was performed by general solid phase synthesis. The resin (10 mg) and DIEA (0.1 ml) in NMP (0.7 ml) was added each amine (4 eq). The reaction mixture was stirred for 2 hr at 120° C. and filtered. The resin was washed with DMF (3 times), dichloromethane (3 times), methanol (3 times), and dichloromethane (3 times).

The resin cleavage reaction was performed using 10% TFA in dichloromethane for 30 min at room temperature and washed with dichloromethane.

The products were identified by liquid chromatography-mass spectroscopy (Agilent 1100 model).

| Comp. ID | R1 | Exact Mass | Found (M + 1) |
|---|---|---|---|
| | 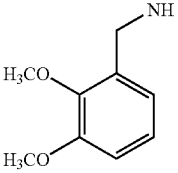 | | |
| S53 | 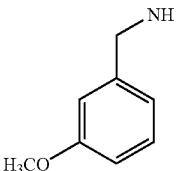 | 478.2 | 479.2 |
| S54 | 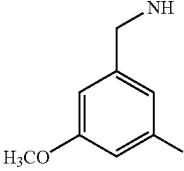 | 436.2 | 437.2 |
| S55 | 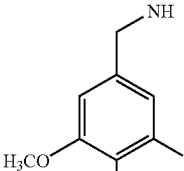 | 478.2 | 479.2 |
| S56 | 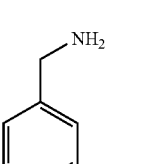 | 448.2 | 449.2 |
| S57 | 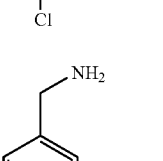 | 478.2 | 479.2 |
| S58 | 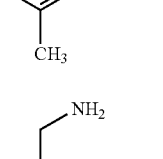 | 508.3 | 509.2 |
| S59 | 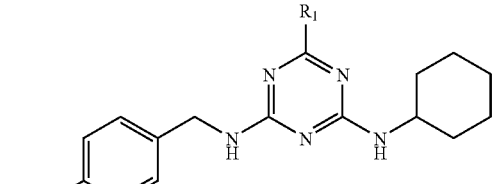 | 452.2 | 453.2 |
| S60 | 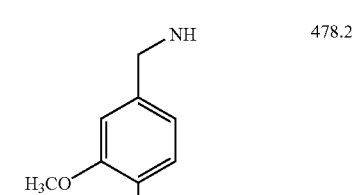 | 432.2 | 433.2 |
| S61 | 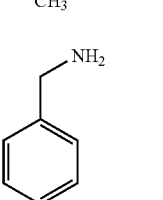 | 502.3 | 503.2 |

-continued
| Comp. ID | R1 | Exact Mass | Found (M + 1) |
|---|---|---|---|
| S62 | 3-fluorobenzylamine | 436.2 | 437.2 |
| S63 | 2-methoxybenzylamine | 448.2 | 449.2 |
| S64 | 2,4-dimethoxybenzylamine | 478.2 | 479.2 |
-continued
| Comp. ID | R1 | Exact Mass | Found (M + 1) |
|---|---|---|---|
| S65 | benzo[1,3]dioxol-5-ylmethylamine | 462.2 | 463.2 |
| S66 | cyclohexylamine | 410.2 | 411.2 |
EXAMPLE 3
Scheme 5
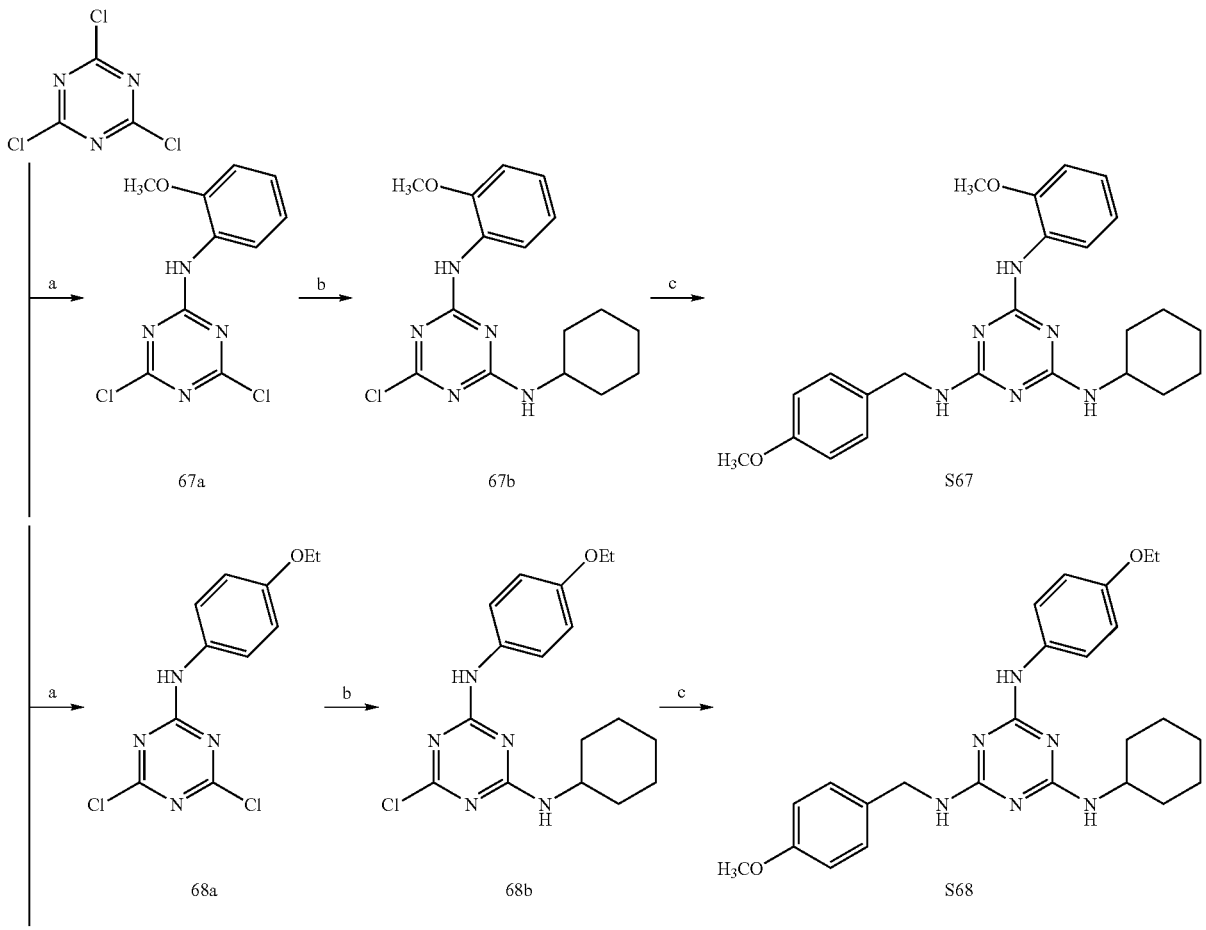

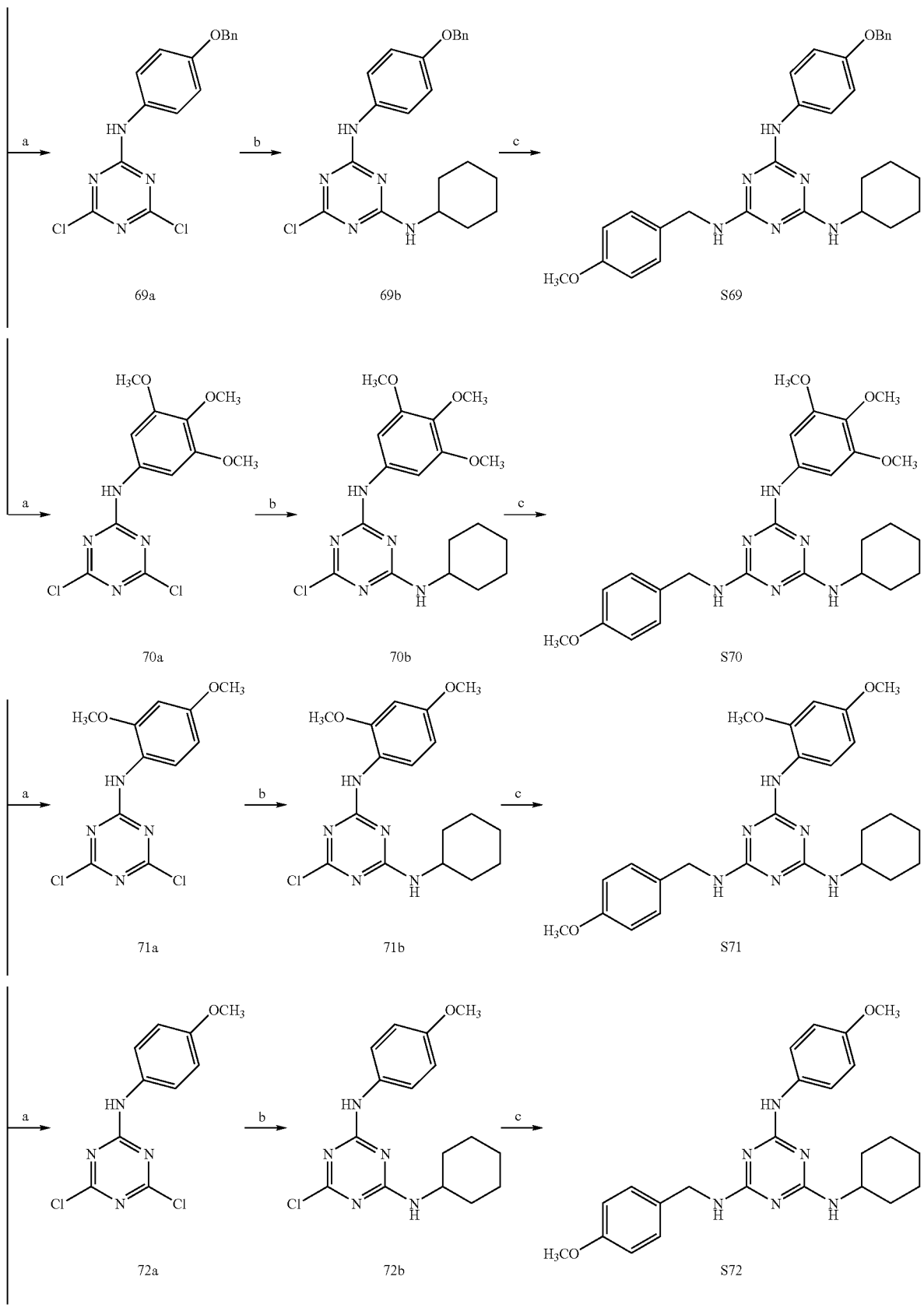

-continued
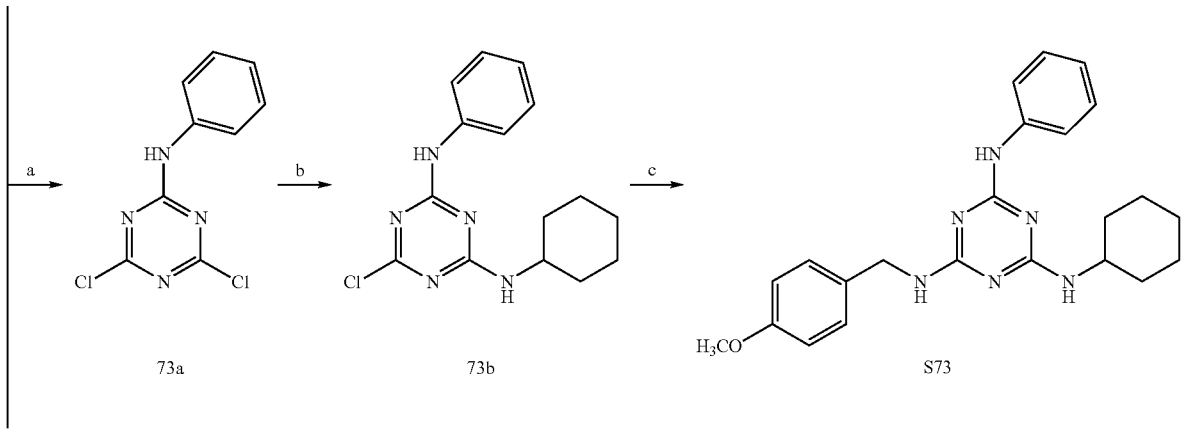
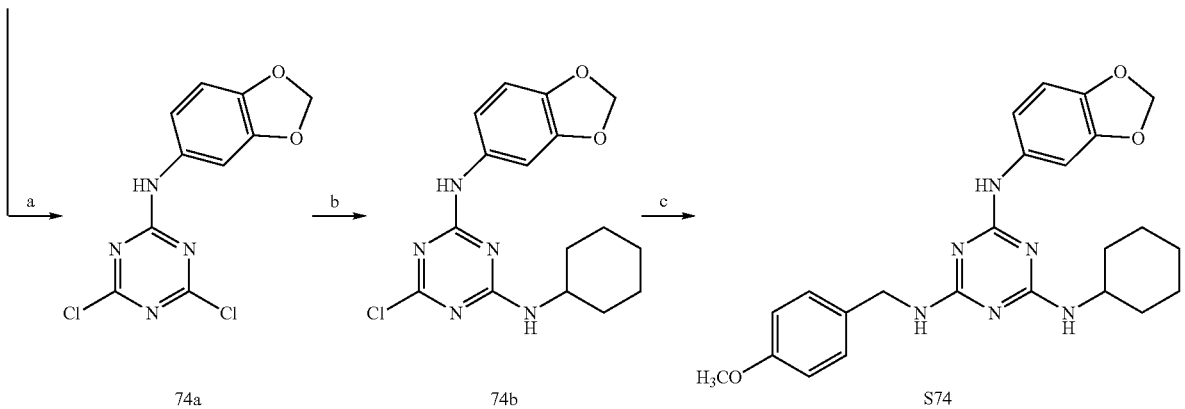
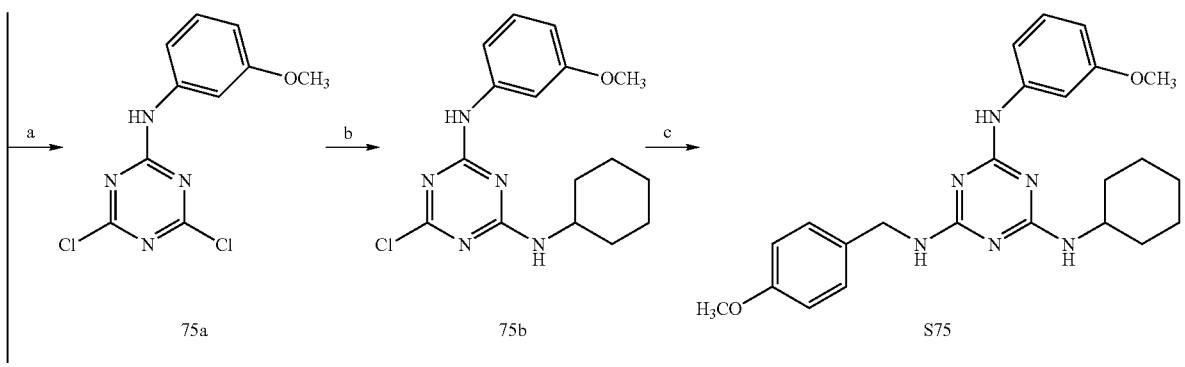

-continued

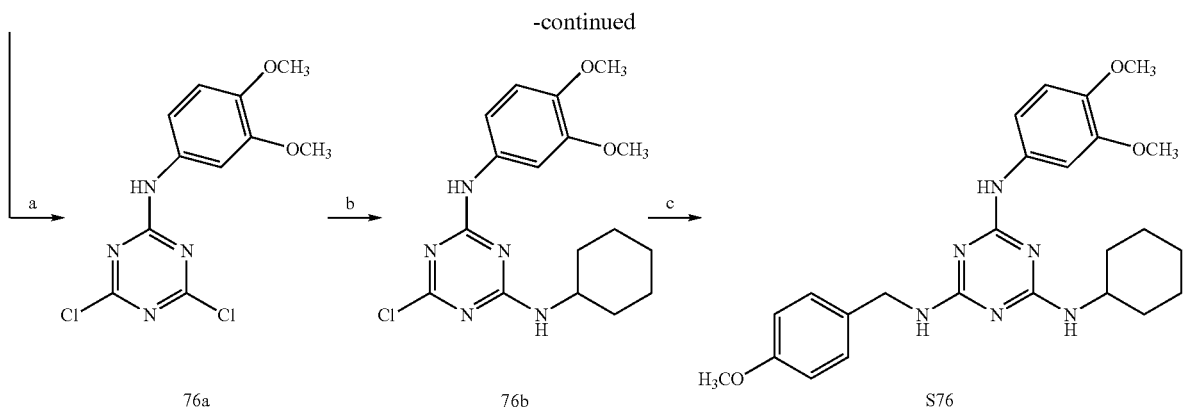

Reagents: (a) 2-Methoxyaniline or 4-ethoxyaniline or 4-phenoxyaniline or 3,4,5-trimethoxyaniline or 2,4-dimethoxyaniline or 4-methoxyaniline or aniline or benzo[1,3]dioxol-5-ylamine or 3-methoxyaniline or 2,3-dimethoxyniline, THF, DIEA, 30 min, 0° C. (b) Cyclohexylamine, THF, DIEA, 3 hr, rt. (c) 4-methoxybenzylamine, THF, 12 hr, 70° C.

Syntheses of Compounds (67a, 68a, 69a, 70a, 71a, 72a, 73a, 74a, 75a, 76a)

To a solution of cyanuric chloride (100 mg, 0.543 mmole, purchased from Acros Chemical Company, USA) and DIEA (0.05 ml, purchased from Aldrich Chemical Company, USA) in anhydrous THF (5 ml, purchased from Aldrich Chemical Company, USA) was added each amine reagent (used 0.652 mmole, 1.2 eq) at 0° C. The reaction mixture was stirred for 30 min at 0° C. After TLC checking, the reaction mixture was filtered and solvent was removed in vacuo. The compounds were purified by column chromatography. Each compound was identified by liquid chromatography-mass spectroscopy (Agilent 1100 model).

Syntheses of Compounds (67b, 68b, 69b, 70b, 71b, 72b, 73b, 74b, 75b, 76b)

To a solution of each synthetic compound (67a, 68a, 69a, 70a, 71a, 72a, 73a, 74a, 75a, 76a) (0.200 mmole) and DIEA (0.02 ml, purchased from Aldrich Chemical Company, USA) in anhydrous THF (5 ml, purchased from Aldrich Chemical Company, USA) was added cyclohexylamine (used 0.240 mmole, 1.2 eq) at room temperature. The reaction mixture was stirred for 3 hr at room temperature. After TLC checking, the reaction mixture was filtered and solvent was removed in vacuo. The compounds were purified by column chromatography. Each compound was identified by liquid chromatography-mass spectroscopy (LC-MS) (Agilent 1100 model).

Synthesis of N-Cyclohexyl-N'-(4-methoxybenzyl)-N"-(2-methoxyphenyl)-[1,3,5]Triazine-2,4,6-triamine (S67)

To a solution of 67b (50 mg, 0.150 mmole and DIEA (0.05 ml, purchased from Aldrich Chemical Company, USA) in anhydrous THF (3 ml, purchased from Aldrich Chemical Company, USA) was added 4-methoxybenzylamine (62 mg, 0.451 mmole, 3.0 eq) at room temperature. The reaction mixture was stirred for 12 hr at 70° C. After TLC checking, the reaction mixture was filtered and solvent was removed in vacuo. The compounds were purified by column chromatography (ethylacetate:hexane=2:1) to give 45 mg (69% yield) of S67 as a colorless oil. LC-MS: Cald. 434.24, Found (M+1) 435.2

Synthesis of N-Cyclohexyl-N'-(4-ethoxyphenyl)-N"-(4-methoxybenzyl)-[1,3,5]Triazine-2,4,6-triamine (S68)

Compound 68b (50 mg, 0.144 mmole) and 4-methoxybenzylamine (60 mg, 0.432 mmole, 3.0 eq) was subjected to the same reaction described for the synthesis of S67 to give 45 mg (70% yield) of S68 as colorless oil. LC-MS: Cald. 448.26, Found (M+1) 449.1.

Synthesis of N-Cyclohexyl-N'-(4-methoxybenzyl)-N"-(4-benzyloxyphenyl)-[1,3,5]Triazine-2,4,6-triamine (S69)

Compound 69b (50 mg, 0.127 mmole) and 4-methoxybenzylamine (52 mg, 0.381 mmole, 3.0 eq) was subjected to the same reaction described for the synthesis of S67 to give 40 mg (62% yield) of S69 as colorless oil. LC-MS: Cald. 510.27, Found (M+1) 511.1.

Synthesis of N-Cyclohexyl-N'-(4-methoxybenzyl)-N"-(3,4,5-trimethoxyphenyl)-[1,3,5]Triazine-2,4,6-triamine (S70)

Compound 70b (50 mg, 0.127 mmole) and 4-methoxybenzylamine (52 mg, 0.381 mmole, 3.0 eq) was subjected to the same reaction described for the synthesis of S67 to give 40 mg (64% yield) of S70 as colorless oil. LC-MS: Cald. 494.26, Found (M+1) 495.2.

Synthesis of N-Cyclohexyl-N'-(2,4-dimethoxyphenyl)-N"-(4-methoxybenzyl)-[1,3,5]Triazine-2,4,6-triamine (S71)

Compound 71b (50 mg, 0.138 mmole) and 4-methoxybenzylamine (57 mg, 0.413 mmole, 3.0 eq) was subjected to the same reaction described for the synthesis of S67 to give 42 mg (66% yield) of S71 as colorless oil. LC-MS: Cald. 464.25, Found (M+1) 465.1.

Synthesis of N-Cyclohexyl-N'-(4-methoxybenzyl)-N"-(4-methoxyphenyl)-[1,3,5]Triazine-2,4,6-triamine (S72)

Compound 72b (50 mg, 0.150 mmole) and 4-methoxybenzylamine (62 mg, 0.451 mmole, 3.0 eq) was subjected to the same reaction described for the synthesis of S67 to give 42 mg (64% yield) of S72 as colorless oil. LC-MS: Cald. 434.24, Found (M+1) 435.2.

Synthesis of N-Cyclohexyl-N'-(4-methoxybenzyl)-N''-phenyl-[1,3,5]Triazine-2,4,6-triamine (S73)

Compound 73b (50 mg, 0.165 mmole) and 4-methoxybenzylamine (68 mg, 0.495 mmole, 3.0 eq) was subjected to the same reaction described for the synthesis of S67 to give 40 mg (60% yield) of S73 as colorless oil. LC-MS: Cald. 404.23, Found (M+1) 405.1.

Synthesis of N-Benzo[1,3]dioxyl-N'-cyclohexyl-N''-(4-methoxybenzyl)-[1,3,5]Triazine-2,4,6-triamine (S74)

Compound 74b (50 mg, 0.144 mmole) and 4-methoxybenzylamine (59 mg, 0.432 mmole, 3.0 eq) was subjected to the same reaction described for the synthesis of S67 to give 38 mg (58% yield) of S74 as colorless oil. LC-MS: Cald. 448.26, Found (M+1) 449.2.

Synthesis of N-Cyclohexyl-N'-(4-methoxybenzyl)-N''-(3-methoxyphenyl)-[1,3,5]Triazine-2,4,6-triamine (S75)

Compound 72b (50 mg, 0.150 mmole) and 4-methoxybenzylamine (62 mg, 0.451 mmole, 3.0 eq) was subjected to the same reaction described for the synthesis of S67 to give 40 mg (61% yield) of S75 as colorless oil. LC-MS: Cald. 434.24, Found (M+1) 435.2.

Synthesis of N-Cyclohexyl-N'-(3,4-dimethoxyphenyl)-N''-(4-methoxybenzyl)-[1,3,5]Triazine-2,4,6-triamine (S76)

Compound 76b (50 mg, 0.138 mmole) and 4-methoxybenzylamine (57 mg, 0.413 mmole, 3.0 eq) was subjected to the same reaction described for the synthesis of S67 to give 43 mg (67% yield) of S76 as colorless oil. LC-MS: Cald. 464.25, Found (M+1) 465.2.

EXAMPLE 4

Scheme 6

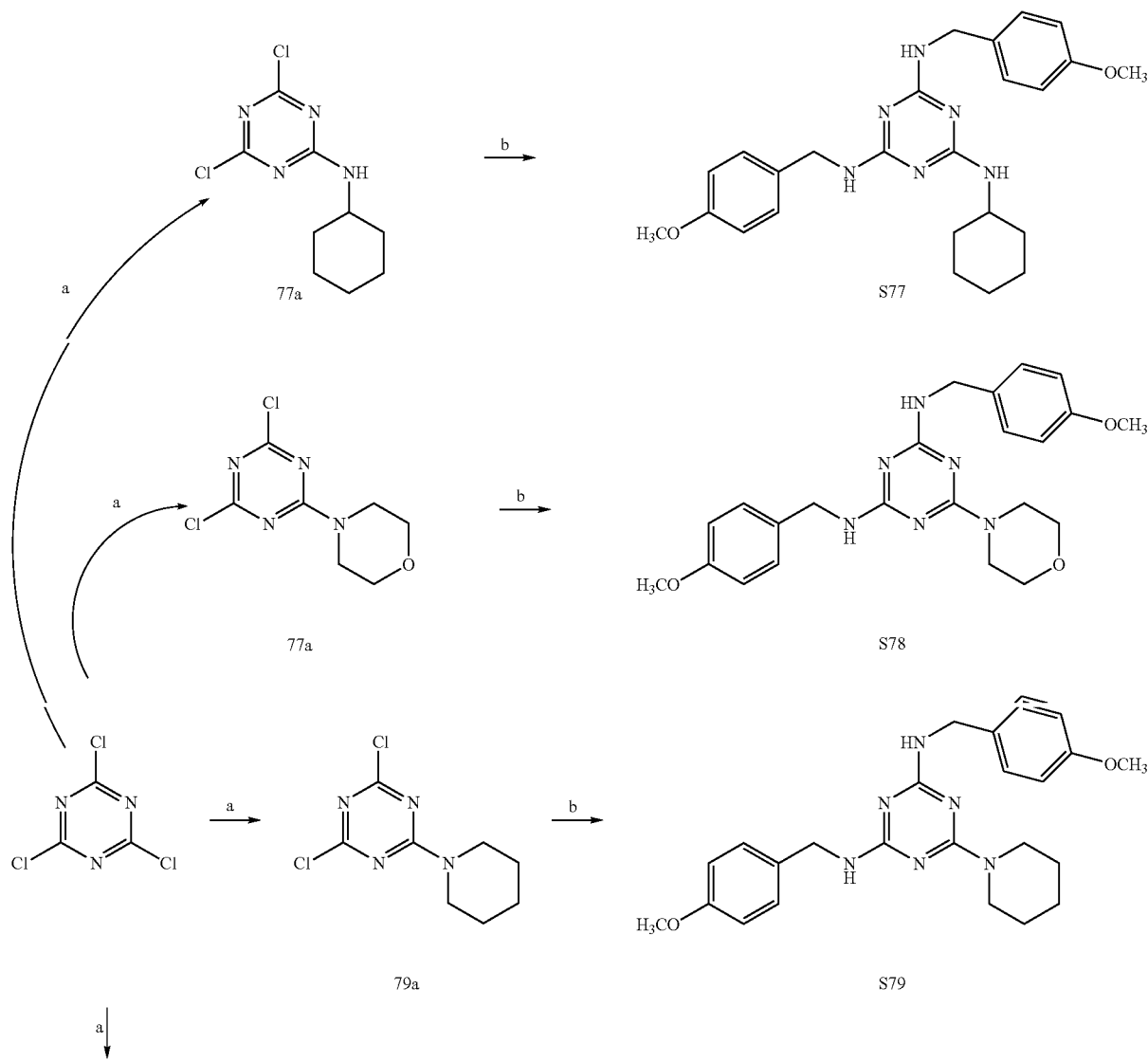

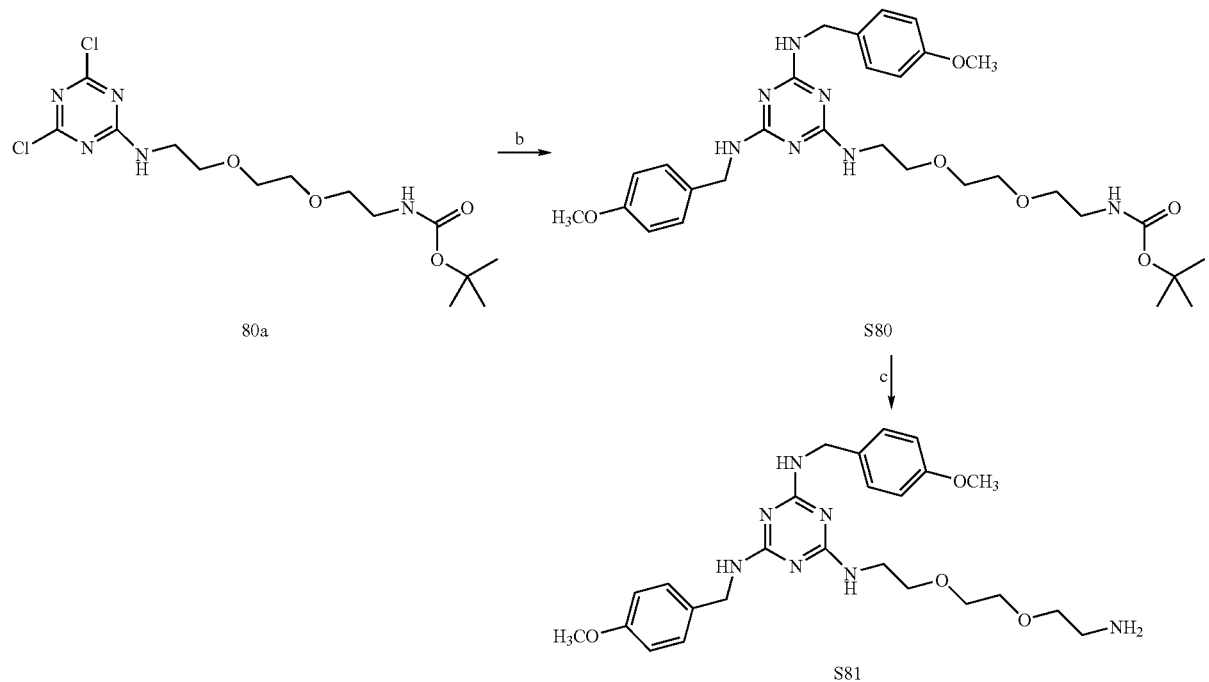
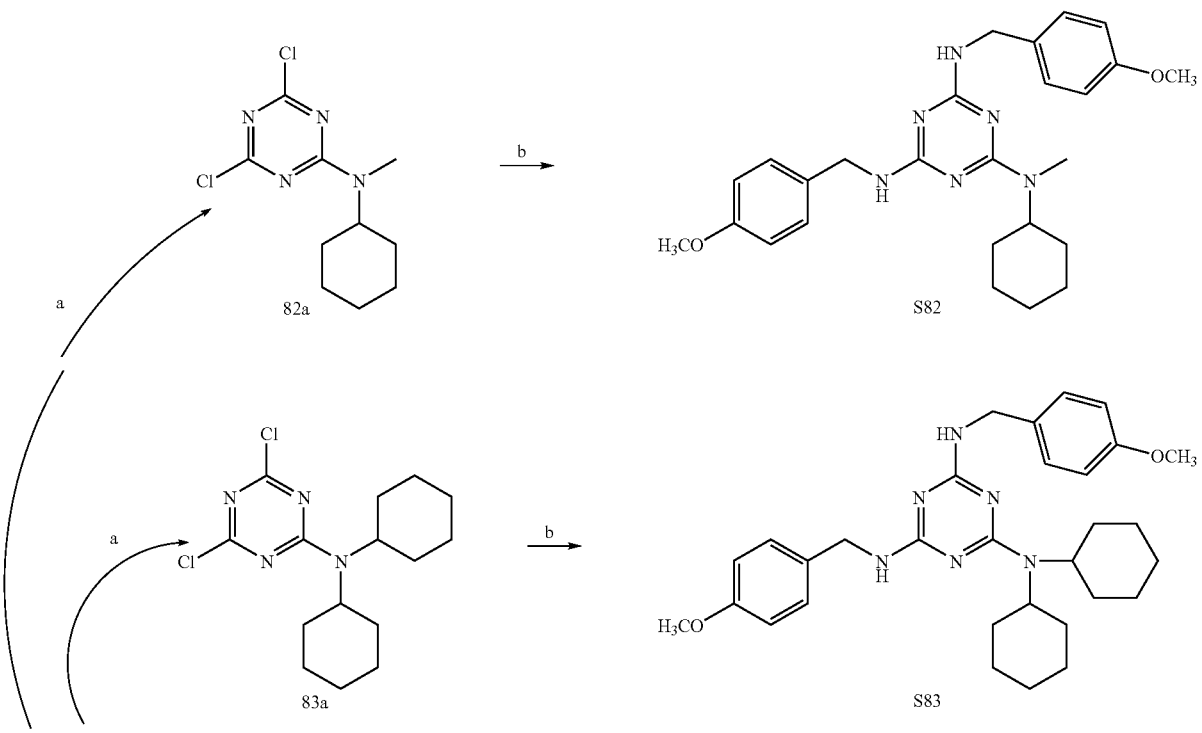
Scheme 7

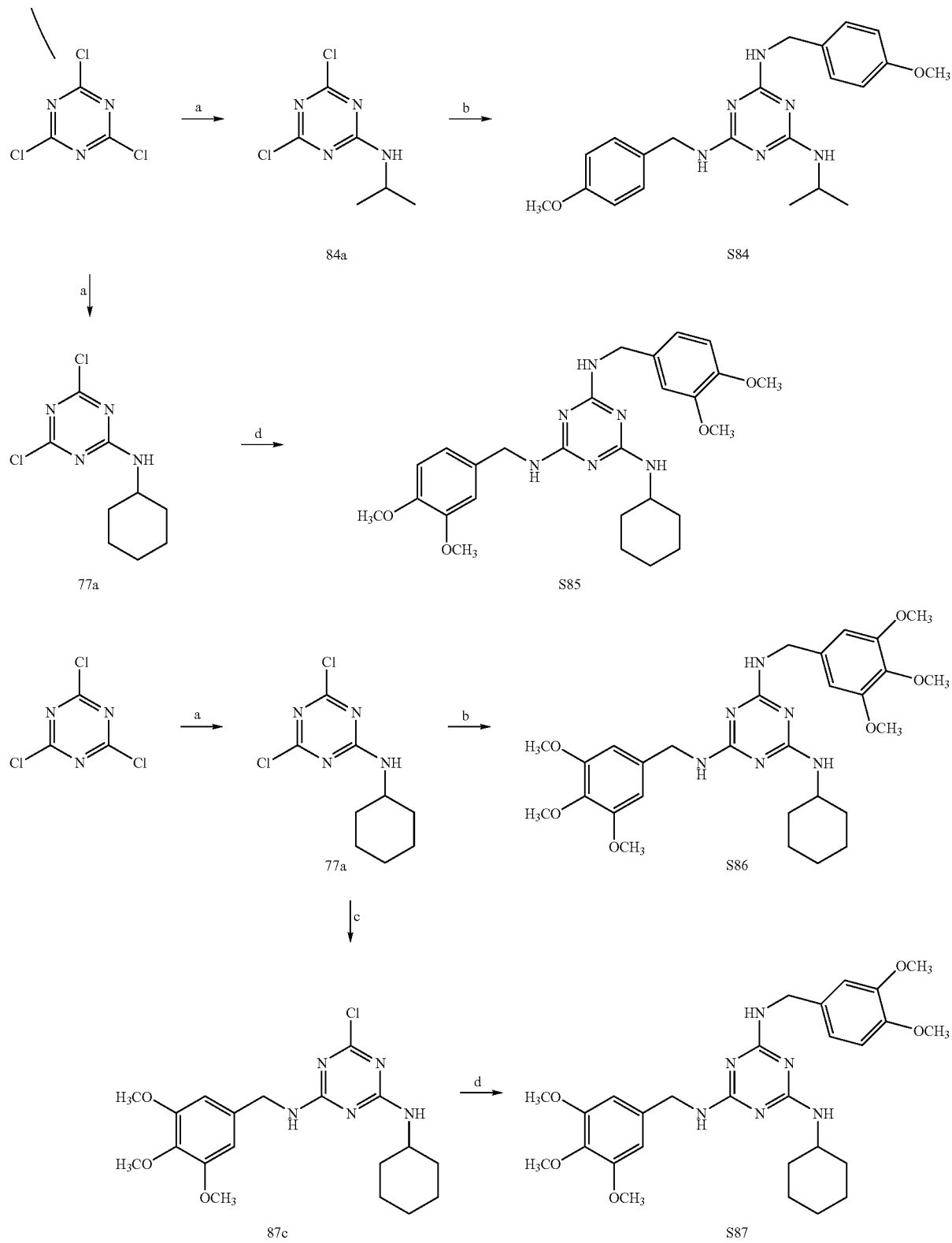
Reagents: (a) Cyclohexylamine, THF, DIEA, 30 min, 0° C. (b) 3,4,5-trimethoxybenzylamine, THF, DIEA, 12 hr, 70° C. (c) 3,4,5-trimethoxybenzylamine, THF, DIEA, 2 hr, rt. (d) 3,4-dimethoxybenzylamine, THF, 12 hr, 70° C.

Syntheses of Compounds (77a, 78a, 79a, 80a, 82a, 83a, 84a)

To a solution of cyanuric chloride (100 mg, 0.543 mmole, purchased from Acros Chemical Company, USA) and DIEA (0.05 ml, purchased from Aldrich Chemical Company, USA) in anhydrous THF (5 ml, purchased from Aldrich Chemical Company, USA) was added each amine reagent (used 0.652 mmole, 1.2 eq) at 0° C. The reaction mixture was stirred for 30 min at 0° C. After TLC checking, the reaction mixture was filtered and solvent was removed in vacuo. The compounds were purified by column chromatography. Each compound was identified by liquid chromatography-mass spectroscopy (Agilent 1100 model).

LC-MS Data

|  | Comp. | | | | | | |
| --- | --- | --- | --- | --- | --- | --- | --- |
|  | 77a | 78a | 79a | 80a | 82a | 83a | 84a |
| Exact Mass | 246.04 | 234.01 | 232.03 | 395.11 | 260.06 | 328.12 | 206.01 |
| Mass (M + 1) | 247.0 | 235.0 | 233.0 | 396.0 | 261.0 | 329.2 | 207.0 |

Synthesis of N-Cyclohexyl-N',N"-bis-(4-methoxybenzyl)-[1,3,5]Triazine-2,4,6-triamine (S77)

To a solution of 77a (100 mg, 0.379 mmole and DIEA (0.05 ml, purchased from Aldrich Chemical Company, USA) in anhydrous THF (5 ml, purchased from Aldrich Chemical Company, USA) was added 4-methoxybenzylamine (208 mg, 1.516 mmole, 4.0 eq) at room temperature. The reaction mixture was stirred for 12 hr at 70° C. After TLC checking, the reaction mixture was filtered and solvent was removed in vacuo. The compounds were purified by column chromatography (ethylacetate:hexane=2:1) to give 130 mg (77% yield) of N-Cyclohexyl-N',N"-bis-(4-methoxybenzyl)-[1,3,5]triazine-2,4,6-triamine (S77) as a colorless oil. $^1$H NMR (CDCl$_3$, 200 MHz) δ 1.25 (m, 6H, —CH$_2$), 1.73 (m, 4H, —CH$_2$), 1.99 (m, 1H), 3.81 (s, 6H, —OCH$_3$), 4.51 (m, 4H), 6.82 (m, 4H, -Ph), 7.28 (m, -Ph). LC-MS: Cald. 448.26, Found (M+1) 449.1.

Synthesis of N',N"-Bis-(4-methoxybenzyl)-6-morpholin-4-yl-[1,3,5]Triazine-2,4-diamine (S78)

Compound 78a (100 mg, 0.407 mmole) and 4-methoxybenzylamine (223 mg, 1.626 mmole, 4.0 eq) were subjected to the same reaction described for the synthesis of S77 to give 140 mg (79% yield) of S78 as colorless oil. $^1$H NMR (CDCl$_3$, 200 MHz) δ 3.70 (m, 8H, —CH$_2$), 3.79 (s, 6H, —OCH$_3$), 4.51 (s, 4H), 5.18 (bs, 2H, each —NH), 6.83 (d, 4H, J=8.7 Hz, -Ph), 7.23 (d, 4H, J=8.5 Hz, -Ph). LC-MS: Cald. 436.22, Found (M+1) 437.1.

Synthesis of N',N"-Bis-(4-methoxybenzyl)-6-piperidin-4-yl-[1,3,5]Triazine-2,4-diamine (S79)

Compound 79a (100 mg, 0.431 mmole) and 4-methoxybenzylamine (236 mg, 1.723 mmole, 4.0 eq) were subjected to the same reaction described for the synthesis of S77 to give 140 mg (75% yield) of S79 as colorless oil. LC-MS: Cald. 434.24, Found (M+1) 435.2.

Synthesis of [2-(2-{2-[4,6-Bis-(4-methoxybenzylamino)-[1,3,5]Triazine-2-ylamino]-ethoxy}-ethyl)-carbamic acid tert-butyl ester (S80)

Compound 80a (100 mg, 0.253 mmole) and 4-methoxybenzylamine (140 mg, 1.012 mmole, 4.0 eq) were subjected to the same reaction described for the synthesis of S77 to give 100 mg (66% yield) of S80 as colorless oil. $^1$H NMR (CDCl$_3$, 200 MHz) δ 1.40 (s, 9H, —CH$_3$), 3.31 (m, 4H, —CH$_2$), 3.54 (m, 8H, —CH$_2$), 3.79 (s, 6H, —OCH$_3$), 4.49 (s, 2H), 4.51 (s, 2H), 5.20 (bs, 2H, each —NH), 6.82 (d, 4H, J=8.3 Hz, -Ph), 7.21 (d, 4H, J=8.1 Hz, -Ph). LC-MS: Cald. 597.33, Found (M+1) 598.2.

Synthesis of N-{2-[2-(2-Amino-ethoxy)ethyl]-N',N"-bis-(4-methoxybenzyl)-[1,3,5]Triazine-2,4,6-triamine (S81)

The compound S80 (50 mg, 0.084 mmole) was soluble in THF (5 ml) and added conc.HCl (0.025 ml). The reaction mixture was stirred for 30 min at 50° C., and then neutralized with 10% sodium bicarbonate solution. The reaction mixture was extracted with ethylacetate and water. The organic layer was washed with brine, dried over anhydrous MgSO$_4$ and filtered. After evaporation of solvent, the product was purified by column chromatography to give 100 mg (66% yield) of S81 as colorless oil. $^1$H NMR (CDCl$_3$, 200 MHz) δ 2.44 (bs, 2H, —CH$_2$), 2.88 (bs, 2H, —CH$_2$), 3.59 (m, 8H, —CH$_2$), 3.78 (s, 6H, —OCH$_3$), 4.47 (s, 4H), 6.83 (d, 4H, J=8.2 Hz, -Ph), 7.21 (d, 4H, J=8.1 Hz, -Ph). LC-MS: Cald. 497.28, Found (M+1) 498.2.

Synthesis of N-Cyclohexyl-N',N"-bis-(4-methoxybenzyl)-N-methyl-[1,3,5]Triazine-2,4,6-triamine (S82)

Compound 82a (100 mg, 0.384 mmole) and 4-methoxybenzylamine (211 mg, 1.53 mmole, 4.0 eq) were subjected to the same reaction described for the synthesis of S77 to give 130 mg (73% yield) of S82 as colorless oil. LC-MS: Cald. 462.27, Found (M+1) 463.1.

Synthesis of N,N-Dicyclohexyl-N',N"-bis-(4-methoxybenzyl)-[1,3,5]Triazine-2,4,6-triamine (S83)

Compound 83a (100 mg, 0.305 mmole) and 4-methoxybenzylamine (167 mg, 1.22 mmole, 4.0 eq) were subjected to the same reaction described for the synthesis of S77 to give 100 mg (62% yield) of S83 as colorless oil. LC-MS: Cald. 530.34, Found (M+1) 531.2.

Synthesis of N-Isopropyl-N',N"-bis-(4-methoxybenzyl)-[1,3,5]Triazine-2,4,6-triamine (S84)

Compound 84a (100 mg, 0.485 nmole) and 4-methoxybenzylamine (270 mg, 1.94 mmole, 4.0 eq) were subjected to the same reaction described for the synthesis of S77 to give 140 mg (71% yield) of S84 as colorless oil. LC-MS: Cald. 408.23, Found (M+1) 409.2.

Synthesis of N-Cyclohexyl-N',N''-bis-(3,4-dimethoxybenzyl)-[1,3,5]Triazine-2,4,6-triamine (S85)

Compound 77a (100 mg, 0.379 mmole) and 3,4-dimethoxybenzylamine (235 mg, 1.516 mmole, 4.0 eq) were subjected to the same reaction described for the synthesis of S77 to give 110 mg (57% yield) of S85 as colorless oil. LC-MS: Cald. 508.28, Found (M+1) 509.2.

Synthesis of N-Cyclohexyl-N',N''-bis-(3,4,5-trimethoxybenzyl)-[1,3,5]Triazine-2,4,6-triamine (S86)

Compound 77a (100 mg, 0.379 mmole) and 3,4,5-dimethoxybenzylamine (300 mg, 1.516 mmole, 4.0 eq) were subjected to the same reaction described for the synthesis of S77 to give 120 mg (56% yield) of S86 as colorless oil. LC-MS: Cald. 568.30, Found (M+1) 569.2.

Synthesis of N-Cyclohexyl-N'-(3,4-dimethoxy)-N''-(3,4,5-trimethoxybenzyl)-[1,3,5]Triazine-2,4,6-triamine (S87)

To a solution of 77a (100 mg, 0.379 mmole) and DIEA (0.05 ml) in anhydrous THF (10 ml) was added 3,4,5-dimethoxybenzylamine (94 mg, 0.476 mmole, 1.2 eq). The reaction mixture was stirred for 2 hr at room temperature. After TLC checking, the reaction mixture was filtered and solvent was removed in vacuo. The compounds were purified by column chromatography (ethylacetate:hexane=1:2) to give 140 mg (90% yield) of 87c as a colorless oil. LC-MS: Cald. 407.27, Found (M+1) 408.1. Compound 87c (100 mg, 0.245 mmole) and 3,4,5-dimethoxybenzylamine (300 mg, 0.735 mmole, 3.0 eq) was subjected to the same reaction described for the synthesis of S77 to give 110 mg (83% yield) of S87 as colorless oil. LC-MS: Cald. 538.29, Found (M+1) 539.2.

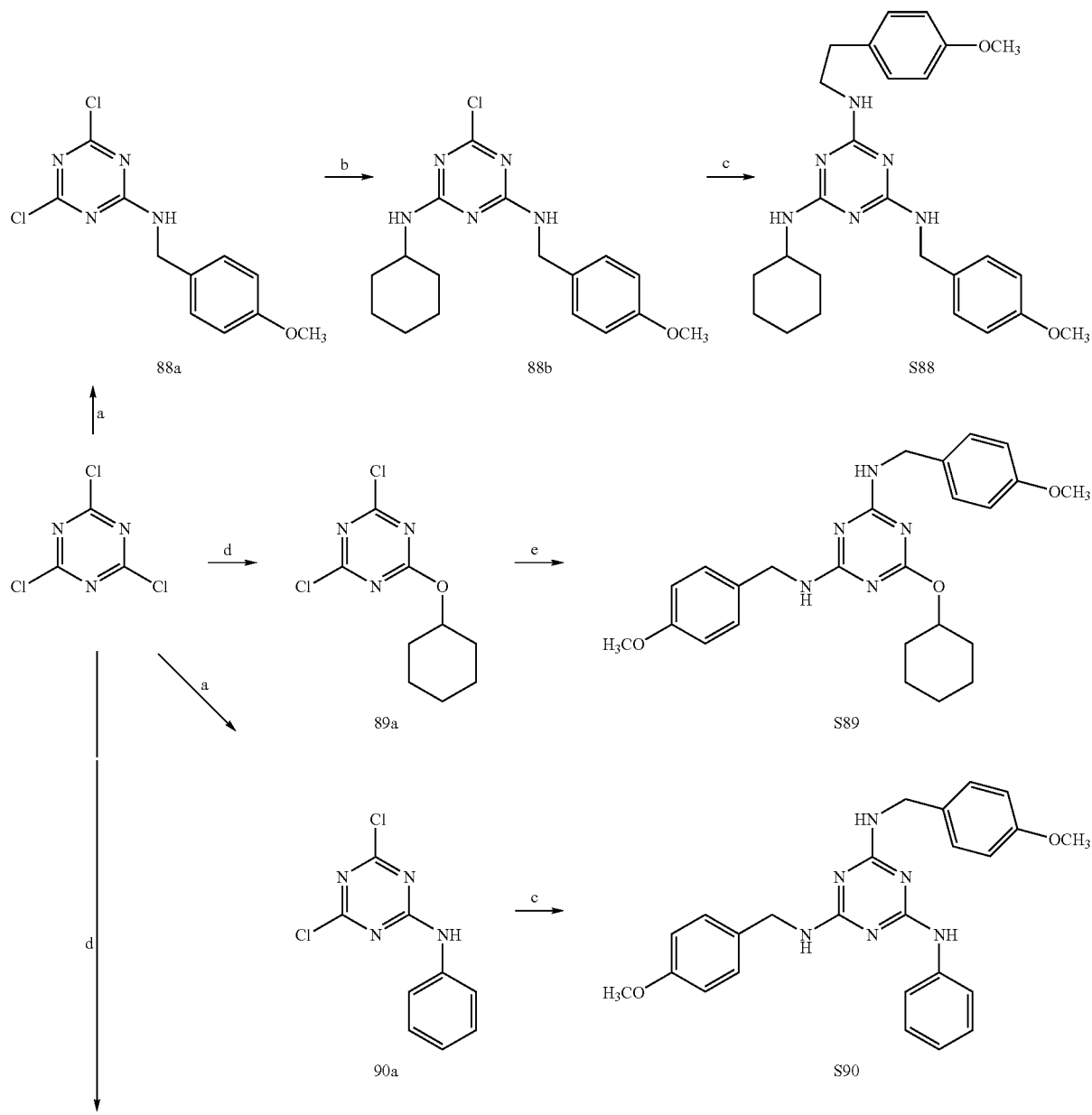

-continued

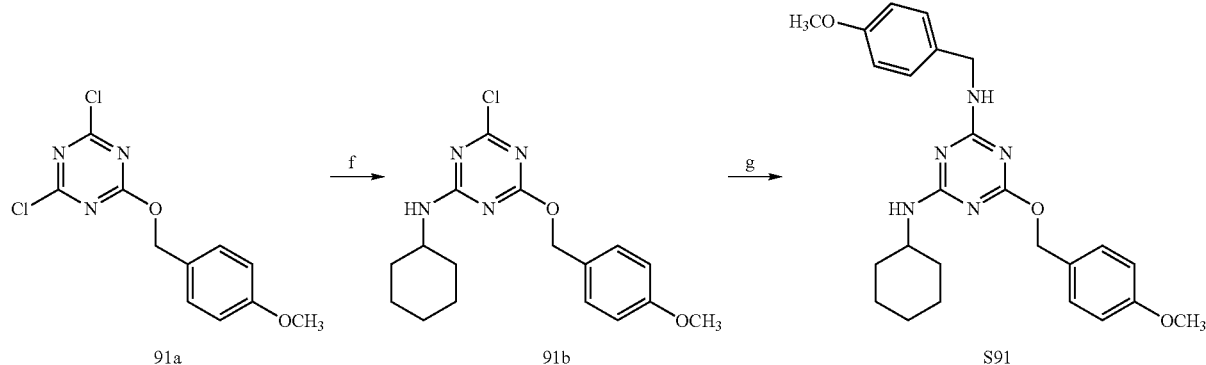

Reagents: (a) 4-Methoxybenzylamine or aniline, THF, DIEA, 30 min, 0° C. (b) cyclohexylamine, THF, DIEA, 2 hr, rt. (c) 4-methoxyphenethylamine or 4-methoxybenzylamine, THF, 12 hr, 70° C. (d) cyclohexanol, or 4-methoxybenzyl alchol, K₂CO₃, 12 hr, 80° C. (e) 4-methoxybenzylamine, THF, 12 hr, 70° C. (f) cyclohexylamine, THF, DIEA, 2 hr, rt. (g) 4-methoxybenzylamine, THF, 12 hr, 70° C.

Synthesis of N-Cyclohexyl-N'-(4-methoxybenzyl)-N''-(4-methoxyphenethyl)-[1,3,5]triazine-2,4,6-triamine (S88)

Compound 88b (50 mg, 0.144 mmole) and 4-methoxyphenethylamine (59 mg, 0.413 mmole, 3.0 eq) were subjected to the same reaction described for the synthesis of S67 to give 42 mg (66% yield) of S88 as colorless oil. LC-MS: Cald. 462.27, Found (M+1) 463.1.

Synthesis of 6-Cyclohexyloxy-N,N'-bis-(4-methoxybenzyl)-[1,3,5]Triazine-2,4-diamine (S89)

To a solution of cyanuric chloride (100 mg, 0.543 mmole and DIEA (0.05 ml) in anhydrous THF was added cyclohexanol (65 mg, 0.653 mmole, 1.2 eq) at room temperature. The reaction mixture was stirred for 12 hr at 80° C. After TLC checking, the reaction mixture was filtered and solvent was removed in vacuo. The compounds were purified by column chromatography (ethylacetate:hexane=1:7) to give 80 mg, (59% yield) of 89a as a colorless oil. The compound 89a (50 mg, 0.122 mmole) was soluble in THF and to this were added DIEA (0.02 ml), 4-methoxybenzylamine (85 mg, 0.617 mmole, 3 eq). The reaction mixture was stirred for 12 hr at 80° C. After TLC checking, the reaction mixture was filtered and solvent was removed in vacuo. The compounds were purified by column chromatography (ethylacetate:hexane=1:1) to give 40 mg (73% yield) of S89 as a colorless oil. LC-MS: Cald. 449.24, Found (M+1) 450.1.

Synthesis of N,N'-Bis(4-methoxybenzyl)-N''-phenyl-[1,3,5]Triazine-2,4,6-triamine (S90)

Compound 90a (50 mg, 0.208 mmole) and 4-methoxyphenethylamine (86 mg, 0.624 mmole, 3.0 eq) were subjected to the same reaction described for the synthesis of S67 to give 62 mg (67% yield) of S90 as colorless oil. LC-MS: Cald. 442.21, Found (M+1) 443.1.

Synthesis of N-Cyclohexyl-N'-(4-methoxybenzyl)-6-(4-methoxy-benzyloxy)-[1,3,5]Triazine-2,4-diamine (S91)

To a solution of cyanuric chloride (100 mg, 0.543 mmole and DIEA (0.05 ml) in anhydrous THF was added 4-methoxybenzyl alcohol 68 mg, 0.660 mmole, 1.2 eq) at room temperature. The reaction mixture was stirred for 12 hr at 80° C. After TLC checking, the reaction mixture was filtered and solvent was removed in vacuo. The compounds were purified by column chromatography (ethylacetate:hexane=1:7) to give 0.86 mg (63% yield) of 91a as a colorless oil. After attaching cyclohexylamine (91c) as similar method with 67b, the compound 91c (50 mg, 0.144 mmole) was soluble in THF and added DIEA (0.02 ml), 4-methoxybenzylamine (40 mg, 0.290 mmole, 2.0 eq). The reaction mixture was stirred for 12 hr at 80° C. After TLC checking, the reaction mixture was filtered and solvent was removed in vacuo. The compounds were purified by column chromatography (ethylacetate:hexane=1:7) to give 50 mg (77% yield) of S91 as a colorless oil. LC-MS: Cald. 449.24, Found (M+1) 450.1.

Zebrafish Screening

Embryos were grown in 96 well tissue-culture plates, containing 2-3 embryos, 250 µl of Hanks-derived buffer, 1% DMSO, and a 40 µM concentration of a single compound from a carbohydrate mimetic library per well. During the development, in order to accurately assess when a chemical takes effect, embryos were exposed to each compound at two discrete timepoints, 1K stage (pre-gastrulation) and at 2S (postgastrulation).

Embryos were visually examined, under a dissecting microscope, up to 72 hr post-exposure. Phenotypes that were desired include defects in general body shape, delays in growth, defects in gastrulation, and in embryonic structures, such as the notochord and somites, as well as defects in circulation. Compounds causing general necrosis of the embryos were considered to be acting nonspecifically and were not examined further. Embryos expressing a specific phenotype were photographed using a M2BioAxiocam dissecting scope.

In Vitro Microtubule Disassembly Assay

Reagent A was made by mixing 250 mg/25 mL tubulin and rhodamine-tubulin (60 mg/6 mL), purchased from Cytoskeleton, with 20 mL, 10 mM GTP at 0° C. Reagent B was made by dissolving the compounds (various concentrations, 2 mL in DMSO) in 2×assay buffer (200 mL, 80 mM K PIPES (pH 7.5), 5 mM MgCl₂, 1 mM EDTA). Two mL of Reagent A and two mL of Reagent B were mixed in a 500 mL E-tube and incubated at 37° C. for 20 minutes. Then, 100 uL of 60% glycerol was added and mixed by gently pipetting the mixture up and down three times. Two uL of the mixture was placed onto a glass slide, covered with a coverslip, and observed by fluorescence microscopy (400×magnification, rhodamine channel).

Growth Inhibition of Cancer Cells

Human U937 leukemia cells were obtained from ATCC. Cells were grown in proliferation media (RPMI-1640 plus 2.38 g/L HEPES, 4.5 g/L glucose, 1.5 g/L NaHCO$_3$, 0.3 g/L Glutamine, 0.11 g Na Pyruvate) plus 20% fetal calf serum. Cells were kept at 37° C., 5% CO$_2$, at a concentration of 0.2-1×10$^6$ cells/ml. To a 100 µl cell suspension in 96-well plate (1×10$^4$ cells/well), 20 µl of MTS tetrazolium reagent solution (Promega) in RPMI-1640 medium was added for 2 hours at 37° C. in a 5% CO$_2$ atmosphere. After the incubation period, the reduced formazan product was measured at 490 nm using a plate reader.

TABLE 1

Active compounds with activity

| Compounds | IC50 (tubulin) | IC50 (Cancer cell growth inhibition) |
| --- | --- | --- |
| S1  | 8 µM   | 10 µM |
| S17 | <20 µM | 10 µM |
| S22 | <20 µM | 25 µM |
| S25 | <20 µM | 25 µM |
| S33 | <20 µM | 18 µM |
| S34 | <20 µM | 20 µM |
| S43 | <20 µM | 12 µM |
| S51 | <20 µM | 20 µM |
| S53 | 2.5 µM | 1 µM |
| S77 | <20 µM | 5 µM |
| S78 | <20 µM | 12 µM |
| S84 | <20 µM | 9 µM |

The compounds of the present invention can be used alone or in combination with known anti-cancer drugs for anti-tumor and anti-proliferation.

Pharmaceutical compositions according to the present invention can be administered by any convenient route, including parenteral, subcutaneous, intravenous, intramuscular, intra peritoneal, or transdermal. Alternatively or concomitantly, administration may be by the oral route. The dosage administered depends upon the age, heath, and weight of the recipient, nature of concurrent treatment, if any, and the nature of the effect desired.

Compositions within the scope of the present invention include all compositions wherein the active ingredient is contained in an amount effective to achieve its intended purpose. While individual needs vary, determination of optimal ranges of effective amounts of each compound is within the skill of the art. Typical dosages comprise 0.01 to 100 mg/kg body weight. The preferred dosages comprising 0.1 to 100 mg/kg body weight. The most preferred dosages comprise 1 to 50 mg/kg body weight.

Pharmaceutical compositions for administering the active ingredients of the present invention preferably contain, in addition to the pharmacologically active compound, suitable pharmaceutically acceptable carriers comprising excipients and auxiliaries which facilitate processing of the active compounds into preparations which can be used pharmaceutically. Preferably, the preparations, particularly those preparations which are administered orally and which can be used for the preferred type of administration, such as tablets, dragees, and capsules, and also preparations which can be administered rectally, such as suppositories, as well as suitable solutions for administration by injection or orally, contain from about 0.01 to about 99 percent by weight, preferably from about 20 to 75 percent by weight, active compound(s), together with the excipient. For purposes of the present invention, all percentages are by weight unless otherwise indicated. In addition to the following described pharmaceutical composition, the compounds of the present invention can be formulated as inclusion complexes, such as cyclodextrin inclusion complexes.

Examples of pharmaceutically acceptable acid addition salt for use in pharmaceutical compositions according to the present invention include those derived from mineral acids, such as hydrochloric, hydrobromic, phosphoric, metaphosphoric, nitric, and sulfuric acids, and organic acids such as tartaric, acetic, citric, malic, lactic, fumaric, benzoic, glycolic, gluconic, succinic, and arylsulfonic, such as p-toluenesulfonic, acids.

The pharmaceutically acceptable carriers include vehicles, adjuvants, excipients, or diluents that are well known to those skilled in the art and which are readily available. It is preferred that the pharmaceutically acceptable carrier be one which is chemically inert to the active compounds and which has no detrimental side effects or toxicity under the conditions of use.

The choice of carrier is determined partly by the particular active ingredient, as well as by the particular method used to administer the composition. Accordingly, there is a wide variety of suitable formulations of the pharmaceutical compositions of the present invention. Formulations can be prepared for oral, aerosol, parenteral, subcutaneous, intravenous, intra arterial, intramuscular, intra peritoneal, intra tracheal, rectal, and vaginal administration.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders such as starch paste using, for example, maize starch, wheat starch, rice starch, potato starch, gelatin, tragacanth, methyl cellulose, hydroxypropylmethylcellulose, sodium catrboxymethylcelullose, and/or polyvinyl pyrrolidone.

Suitable formulations or parenteral administration include aqueous solutions of the active compounds in water-soluble form, such as water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension, including, for example, sodium carboxymethyl cellulose, sorbitol, and/or dextran. Optionally, the suspension may also contain stabilizers.

Other pharmaceutically acceptable carriers for the active ingredients according to the present invention are liposomes, pharmaceutical compositions in which the active ingredient is contained either dispersed or variously present in corpuscles contained either dispersed or variously present in corpuscles consisting of aqueous concentric layers adherent to lipid layers. The active ingredient may be present both in the aqueous layer and in the lipidic layer, inside or outside, or, in any event, in the non-homogeneous system generally known as a liposomic suspension.

The hydrophobic layer, or lipid layer, generally, but not exclusively, comprises phospholipids such as lecithin and sphingomyelin, steroids such as cholesterol, more or less ionic surface active substances such as dicetyl phosphate, stearylamine, or phosphatidic acid, and/or other materials of a hydrophobic nature.

The compounds may also be formulated for transdermal administration, for example in the form of transdermal patches so as to achieve systemic administration.

Formulations suitable for oral administration can consists of liquid solutions such as effective amounts of the compound(s) dissolved in diluents such as water, saline, or orange juice; capsules, tables, sachets, lozenges, and troches, each containing a predetermined amount of the active ingredient as solids or granules; powders, suspensions in an appropriate liquid; and suitable emulsions. Liquid formulations may include diluents such as water and alcohols, e.g., ethanol, benzyl alcohol, and the polyethylene alcohols, either with or without the addition of a pharmaceutically acceptable surfactant, suspending agents, or emulsifying agents. Capsule forms can be of the ordinary hard- or soft-shelled gelatin type containing, for example, surfactants, lubricant, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscaramellose sodium, talc, magnesium stearate, calcium stearate, zinc stearate, stearic acid, and other preservatives, flavoring agents, and pharmaceutically acceptable disintegrating agents, moistening agents preservatives flavoring agents, and pharmacologically compatible carriers. Lozenge forms can comprise the active ingredient in a carrier, usually sucrose and acacia or tragacanth, as well as pastilles comprising the active ingredient in an inert base such as gelatin or glycerin, or sucrose and acacia. Emulsions and the like can contain, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds can be administered in a physiologically acceptable diluent in a pharmaceutical carriers, such as a sterile liquid or mixture of liquids, including water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethylene glycol) 400, oils, fatty acids, fatty acid esters or glycerides, or acetylated fatty acid glycerides, without the addition of a pharmaceutically acceptable surfactants, such as soap or a detergent, suspending agent, such as carbomers, methylcellulose, hydroxypropylmethylcellulose, or carboxymethylcellulose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Fatty acids can be used in parenteral formulations, including oleic acid, stearic acid, and isostearic acid. Ethyl oleate and isopropyl myristate are examples of suitable fatty acid esters. Suitable salts for use in parenteral formulations include fatty alkali metal, ammonium, and triethanolamine salts, and suitable detergents include cationic detergents such as dimethyl dialkyl ammonium halides, and alkyl pyridimium halides; anionic detergents such as dimethyl olefin sulfonates, alkyl, olefin, ether, and monoglyceride sulfates and sulfosuccinates; polyoxyethylenepolypropylene copolymers; amphoteric detergents such as alkyl-beta-aminopropionates and 2-alkyl-imidazoline quaternary ammonium salts; and mixtures thereof.

Parenteral formulations typically contain from about 0.5 to 25% by weight of the active ingredient in solution. Suitable preservatives and buffers can be used in these formulations. In order to minimize or eliminate irritation at the site of injection, these compositions may contain one or more nonionic surfactants having a hydrophilic-lipophlic balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be present in unit dose or multiple dose sealed containers, such as ampoules and vials, and can be stored in a freeze-dried (lyophilized) condition requiring only the addition of the sterile liquid carrier, e.g., water, for injections immediately prior to use. Extemporaneous injection solutions and suspensions can be prepared from sterile powders, granules, and tablets of the kind previously described.

Additionally, the active ingredients can be formulated into suppositories by mixing the active ingredient with a variety of bases, including emulsifying bases or water-soluble bases. Formulations suitable for vaginal administration may be in the form of pessaries, tampons, creams, gels, pastes, foam, or spray formulations containing, in addition to the active ingredient, such carriers as are known in the art to be appropriate.

The active ingredients can be used as functionalized congeners for coupling to other molecules, such as amines and peptides. The use of such congeners provides for increased potency, prolonged duration of action, and prodrugs. Water solubility is also enhanced, which allows for reduction, if not complete elimination, of undesirable binding to plasma proteins and partition in to lipids. Accordingly, improved pharmacokinetics can be realized.

Any number of assays well known in the art may be used to test whether a particular compound suspected of being an anti-tubulin agent.

In determining the dosages of the trisubstituted triazine to be administered, the dosage and frequency of administration is selected in relation to the pharmacological properties of the specific active ingredients. Normally, at least three dosage levels should be used. In toxicity studies in general, the highest dose should reach a toxic level but be sublethal for most animals in the group. If possible, the lowest dose should induce a biologically demonstrable effect. These studies should be performed in parallel for each compound selected.

Additionally, the $ID_{50}$ level of the active ingredient in question can be one of the dosage levels selected, and the other two selected to reach a toxic level. The lowest dose that dose not exhibit a biologically demonstrable effect. The toxicology tests should be repeated using appropriate new doses calculated on the basis of the results obtained. Young, healthy mice or rats belonging to a well-defined strain are the first choice of species, an the first studies generally use the preferred route of administration. Control groups given a placebo or which are untreated are included in the tests. Tests for general toxicity, as outlined above, should normally be repeated in another non-rodent species, e.g., a rabbit or dog. Studies may also be repeated using alternate routes of administration.

Single dose toxicity tests should be conducted in such a way that signs of acute toxicity are revealed and the mode of death determined. The dosage to be administered is calculated on the basis of the results obtained in the above-mentioned toxicity tests. It may be desired not to continue studying all of the initially selected compounds. Data on single dose toxicity, e.g., $ID_{50}$, the dosage at which half of the experimental animals die, is to be expressed in units of weight or volume per kg of body weight and should generally be furnished for at least two species with different modes of administration. In addition to the $ID_{50}$ value in rodents, it is desirable to determine the highest tolerated dose and/or lowest lethal dose for other species, i.e., dog and rabbit.

When a suitable and presumably safe dosage level has been established as outlined above, studies on the drug's chronic toxicity, its effect on reproduction, and potential mutagenicity may also be required in order to ensure that the calculated appropriate dosage range will be safe, also with regard to these hazards.

Pharmacological animal studies on pharmacokinetics revealing, e.g., absorption, distribution, biotransformation, and excretion of the active ingredient and metabolites are then performed. Using the results obtained, studies on human pharmacology are then designed. Studies of the pharmacodynamics and pharmacokinetics of the compounds in humans should be performed in healthy subjects using the routes of administration intended for clinical use, and can be repeated in patients. The dose-response relationship when different doses are given, or when several types of conjugates or combinations of conjugates and free compounds are given, should be studied in order to elucidate the dose-response relationship (dose vs. plasma concentration vs. effect), the therapeutic range, and the optimum dose interval. Also, studies on time-effect relationship, e.g., studies into the time-course of the effect and studies on different organs in order to elucidate the desired and undesired pharmacological effects of the drug, in particular on other vital organ systems, should be performed.

The compounds of the present invention are then ready for clinical trials to compare the efficacy of the compounds to existing therapy. A dose-response relationship to therapeutic effect and for side effects can be more finely established at this point.

The amount of compounds of the present invention to be administered to any given patient must be determined empirically, and will differ depending upon the condition of the patients. Relatively small amounts of the active ingredient can be administered at first, with steadily increasing dosages if no adverse effects are noted. Of course, the maximum safe toxicity dosage as determined by animal toxicity tests should not be exceeded.

The foregoing description of the specific embodiments will so fully reveal the general nature of the invention that other can, by applying current knowledge, readily modify and/or adapt for various application such specific embodiments without undue experimentation and without departing from the generic concept. Therefore, such adaptations and modifications should and are intended to be comprehended within the meaning and range of equivalents of the disclosed embodiments.

It is to be understood that the phraseology or terminology employed herein is for the purpose of description and not of limitation. The means and materials for carrying out various disclosed functions may take a variety of alternative forms without departing from the invention.

Thus, the expressions Ameans to . . . @ and Ameans for . . . @ as may be found in the specification above and/or in the claims below, followed by a functional statement, are intended to define and cover whatever structural, physical, chemical, or electrical element or structures which may now or in the future exist for carrying out the recited function, whether or nor precisely equivalent to the embodiment or embodiments disclosed in the specification above. It is intended that such expressions be given their broadest interpretation.

REFERENCES

Publications:
ArQule: Incorporation of Carbohydrates and Peptides into Large Triazine-Based Screening Libraries Using Automated Parallel Synthesis. Gustafson, G. R.; Baldino, C. M.; O'Donnel, M. E.; Sheldon, A. Tarsa, R. J.; Verni, C. J.; Coffen, D. L. Tetrahedron 1998, 54, 4051-4065.

Selectide Corporation: Library generation through successive substitution of trichlorotriazine. Stankova, M.; Lebl, M. Mol. Diversity 1996, 2, 75-80.

Arris Pharmaceutical: Johnson, Charles R.; Zhang, Birong; Fantauzzi, Pascal; Hocker, Michael; Yager, Kraig M. Libraries of N-alkylamino heterocycles from nucleophilic aromatic substitution with purification by solid supported liquid extraction. Tetrahedron (1998), 54(16), 4097-4106. CODEN: TETRAB ISSN:0040-4020. CAN 128:308415 AN 1998:233899

Abbott: Hajduk, Philip J.; Dinges, Juergen; Schkeryantz, Jeffrey M.; Janowick, David; Kaminski, Michele; Tufano, Michael; Augeri, David J.; Petros, Andrew; Nienaber, Vicki; Zhong, Ping; Hammond, Rachel; Coen, Michael; Beutel, Bruce; Katz, Leonard; Fesik, Stephen W. Novel Inhibitors of Erm Methyltransferases from NMR and Parallel Synthesis. J. Med. Chem. (1999), 42(19), 3852-3859. CODEN: JMCMAR ISSN:0022-2623. CAN 131:308768 AN 1999:567005

Humboldt-Universitaet: Scharn, Dirk; Wenschuh, Holger; Reineke, Ulrich; Schneider-Mergener, Jens; Germeroth, Lothar. Spatially Addressed Synthesis of Amino- and Amino-Oxy-Substituted 1,3,5-Triazine Arrays on Polymeric Membranes. J. Comb. Chem. (2000), 2(4), 361-369. CODEN: JCCHFF ISSN:1520-4766. CAN 133:135605 AN 2000:355907

Hoffmann-La Roche: Masquelin, Thierry; Meunier, Nathalie; Gerber, Fernand; Rosse, Gerard. Solution- and solid-phase synthesis of combinatorial libraries of trisubstituted 1,3,5-triazines. Heterocycles (1998), 48(12), 2489-2505. CODEN: HTCYAM ISSN:0385-5414. CAN 130:196625 AN 1999:50090

Affymax: Silen J L; Lu A T; Solas D W; Gore M A; MacLean D; Shah N H; Coffin J M; Bhinderwala N S; Wang Y. Tsutsui K T; Look G C; Campbell D A; Hale R L; Navre M; DeLuca-Flaherty C R Screening for novel antimicrobials from encoded combinatorial libraries by using a two-dimensional agar format. ANTIMICROBIAL AGENTS AND CHEMOTHERAPY (1998 Jun), 42(6), 1447-53. Journal code: 6HK. ISSN:0066-4804. DN 98287588 PubMed ID 9624492 AN 1998287588

U. Cambridge: Teng, Su Fern; Sproule, Kenny; Hussain, Abid; Lowe, Christopher R. A strategy for the generation of biomimetic ligands for affinity chromatography. Combinatorial synthesis and biological evaluation of an IgG binding ligand. J. Mol. Recognit. (1999), 12(1), 67-75. CODEN: JMORE4 ISSN:0952-3499. CAN 131:30755 AN 1999:224014

U. Iceland: Filippusson, Horour; Erlendsson, Lyour S.; Lowe, Christopher R. Design, synthesis and evaluation of biomimetic affinity ligands for elastases. J. Mol. Recognit. (2000), 13(6), 370-381, 3 Plates. CODEN: JMORE4 ISSN:0952-3499. CAN 134:174701 AN 2000:857136

Patents:
Abbott 1: Henkin, Jack; Davidson, Donald J.; Sheppard, George S.; Woods, Keith W.; McCroskey, Richard W. Preparation of triazine-2,4-diamines as angiogenesis inhibitors. PCT Int. Appl. (1999), 66 pp. CODEN: PIXXD2 WO 9931088 A1 19990624 CAN 131:58855 AN 1999:404953
Abbott 2: Shock, Richard U. 2-[2-(5-Nitrofuryl)]-4,6-diamino-s-triazine. U.S. Pat. Nos. 2,885,400 19,590,505 CAN 53:94898 AN 1959:94898
ArQule: Coffen, David L.; Hogan, Joseph C., Jr. Synthesis and use of biased arrays. PCT Int. Appl. (1998), 53 pp. CODEN: PIXXD2 WO 9846551 A1 19981022 CAN 129: 302216 AN 1998:706192
Trustees of Boston University: Panek, James S.; Zhu, Bin. Synthesis of aromatic compounds by Diels-Alder reaction on solid support. PCT Int. Appl. (1998), 26 pp. CODEN: PIXXD2 WO 9816508 A2 19980423 CAN 128:308494 AN 1998:251157
ISIS Pharmaceuticals, Inc.: Cook, P. Dan; An, Haoyun. Preparation of compounds or combinatorial libraries of compounds having a plurality of nitrogenous substituents. PCT Int. Appl. (1998), 187 pp. CODEN: PIXXD2 WO 9805961 A1 19980212 CAN 128:180338 AN 1998:112497
Hoffman-La Roche: Huber, Ulrich. Silanyl-triazines as light screening compositions. Eur. Pat. Appl. (1999), 26 pp. CODEN: EPXXDW EP 933376 A2 19990804 CAN 131: 130123 AN 1999:505797

Other References
American Chemical Society: Washington, D.C., 1995; pp 345-368.
Filippusson, H.; Erlendsson, L. S,.; Lowe, C. R. J. Mol. *Recognit.* 2000, 13, 370-381.
Gray, N. S.; Kwon, S.; Schultz, P. G. *Tetrahedron Lett.* 1997, 38, 1161-1164. Gray, N. S.; Wodicka, L.; Thunnissen, A. M.; Norman, T. C.; Kwon, S.; Espinoza, F. H.; Morgan, D. O.; Barnes, G.; LeClerc, S.; Meijer, L.; Kim, S.-H.; Schultz, P. G. Science 1998, 281, 533-538.
Gustafson, G. R.; Baldino, C. M.; O'Donnel, M. E.; Sheldon, A. Tarsa, R. J.; Verni, C. J.; Coffen, D. L. *Tetrahedron* 1998, 54, 4051-4065.
Hajduk, P. J.; Dinges, J.; Schkeryantz, J. M.; Janowick, D.; Kaminski, M.; Tufano, M.; Augeri, D. J.; Petros, A.; Nienaber, V.; Zhong, P.; Hammond, R.; Coen, M.; Beutel, B.; Katz, L.; Fesik, S. W. *J. Med. Chem.* 1999, 42, 3852-3859.
Johnson, C. R.; Zhang, B.; Fantauzzi, P.; Hocker, M.; Yager, K. M. *Tetrahedron* 1998, 54, 4097-4106.
Lu, M. C. In *Cancer Chemotherapeutic Agents*; Foye, W. O. Ed.;
Masquelin, T.; Meunier, N.; Gerber, F.; Rosse, G. Heterocycles 1998, 48, 2489-2505.
Norman, T. C.; Gray, N. S.; Koh, J. T.; Schultz, P. G. *J. Am. Chem. Soc.* 1996, 118, 7430-7431.
Rosania, G. R.; Chang, Y. T.; Perez, O.; Sutherlin, D.; Dong, H.; Lockhart, D. J.; Schultz, P. G. *Nat. Biotechnol.* 2000, 18, 304-308.
Scharn, D.; Wenschuh, H.; Reineke, U.; Schneider-Mergener, J.; Germeroth, L. *J. Comb. Chem.* 2000, 2, 361-369.
Stankova, M.; Lebl, *M. Mol. Diversity* 1996, 2, 75-80.
Silen J. L; Lu A. T.; Solas D. W.; Gore M. A.; MacLean D.; Shah N. H.; Coffin J. M.; Bhinderwala N. S.; Wang Y.; Tsutsui K. T.; Look G. C.; Campbell D. A.; Hale R. L.; Navre M.; DeLuca-Flaherty C. R. *Antimicrob. Agents Chemother.* 1998, 42, 1447-1453.
Teng, S. F.; Sproule, K.; Hussain, A.; Lowe, C. R. *J. Mol. Recognit.* 1999, 12, 67-75.
von Angerer, E. *Curr. Opin. Drug Discov. Devel.* 2000, 3, 575-584.
von Angerer, E. *Exp. Opin. Ther. Patents* 1999, 9, 1069-1081.

What is claimed is:

1. A method for treating a patient suffering from cancer selected from the group consisting of breast, ovarian, lung, squamous cell, adenocarcinoma, gastric, melanoma, and salivary gland cancers comprising administering to said patient an effective amount of a microtubule assembly inhibiting compound to interfere with microtubule assembly, wherein said microtubule assembly inhibiting compound is selected from the group consisting of:

a. compounds of the formula

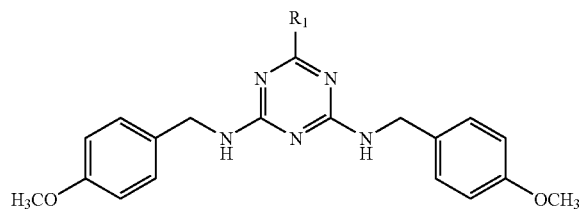

wherein R1 is selected from the group consisting of:

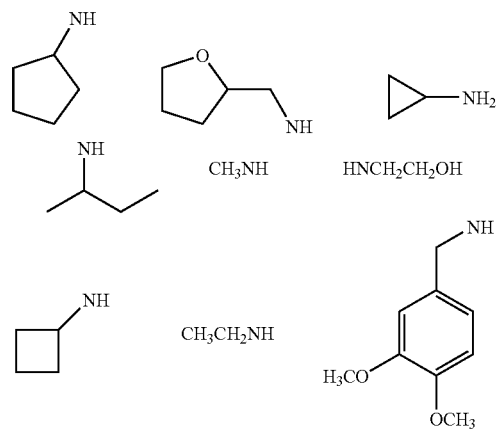

and b. compounds of the formula

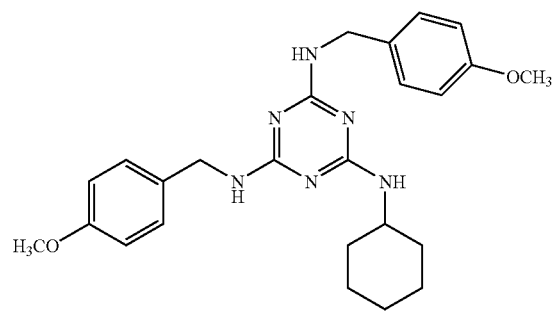

-continued
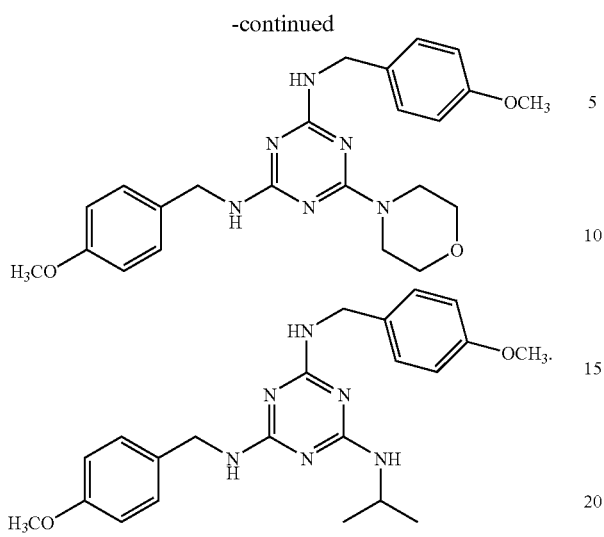
2. A compound that inhibits microtubule assembly formation selected from the group consisting of:
a. compounds of the formula
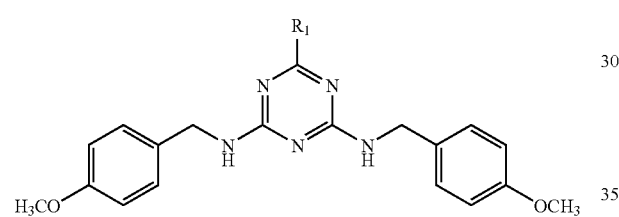
wherein R1 is selected from the group consisting of
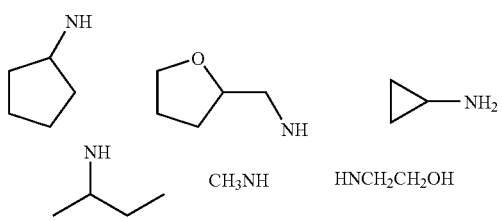
-continued
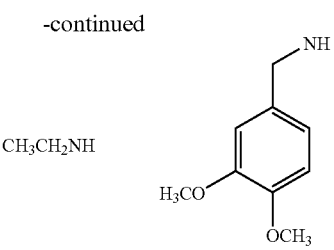
and
b. compounds of the formula
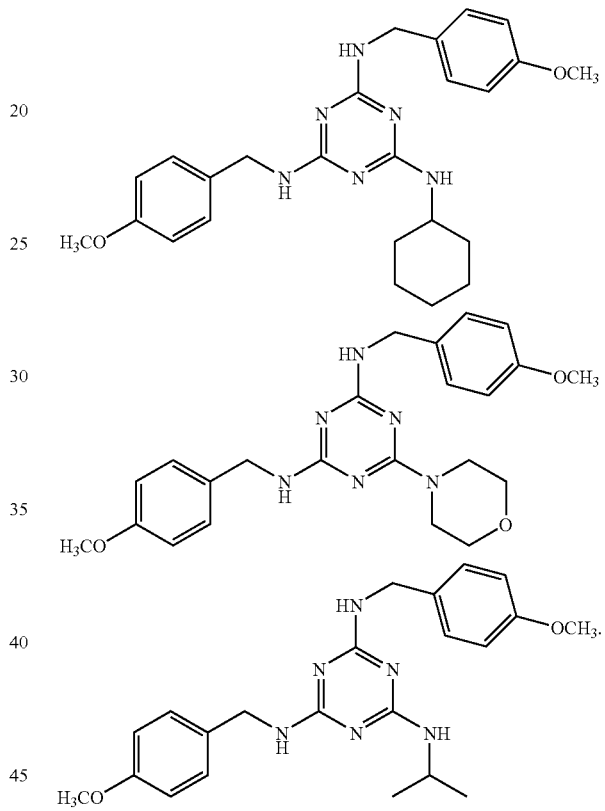
* * * * *